United States Patent
Irvine et al.

(10) Patent No.: US 12,053,759 B2
(45) Date of Patent: Aug. 6, 2024

(54) MIXED OXIDE COMPOSITE COMPRISING CALCIUM OXIDE AND TRICALCIUM ALUMINATE

(71) Applicant: University Court of the University of St Andrews, Fife (GB)

(72) Inventors: John Thomas Sirr Irvine, Fife (GB); Alfredo Bonaccorso, Fife (GB); Despoina Papargyriou, Fife (GB)

(73) Assignee: UNIVERSITY COURT OF THE UNIVERSITY OF ST ANDREWS, Fife (GB)

( * ) Notice: Subject to any disclaimer, the term of this patent is extended or adjusted under 35 U.S.C. 154(b) by 567 days.

(21) Appl. No.: 17/285,789

(22) PCT Filed: Oct. 14, 2019

(86) PCT No.: PCT/GB2019/052921
§ 371 (c)(1),
(2) Date: Apr. 15, 2021

(87) PCT Pub. No.: WO2020/079411
PCT Pub. Date: Apr. 23, 2020

(65) Prior Publication Data
US 2021/0339225 A1    Nov. 4, 2021

(30) Foreign Application Priority Data
Oct. 15, 2018 (GB) .................................... 1816773

(51) Int. Cl.
*B01J 23/04* (2006.01)
*B01J 6/00* (2006.01)
(Continued)

(52) U.S. Cl.
CPC ............... *B01J 23/04* (2013.01); *B01J 6/001* (2013.01); *B01J 23/002* (2013.01); *B01J 35/40* (2024.01);
(Continued)

(58) Field of Classification Search
CPC . B01J 23/04; B01J 6/001; B01J 23/002; B01J 35/023; B01J 35/0006; B01J 35/04;
(Continued)

(56) References Cited

U.S. PATENT DOCUMENTS

| 6,482,387 B1 | 11/2002 | Gulgun et al. |
| 2010/0196259 A1* | 8/2010 | Garg ................. B01J 20/28069 96/108 |
| 2020/0031747 A1* | 1/2020 | Lacoste .................. C07C 29/78 |

FOREIGN PATENT DOCUMENTS

| CN | 101695666 A * | 4/2010 | ............ B01J 27/232 |
| CN | 102500310 A * | 6/2012 | ............ B01D 53/02 |

(Continued)

OTHER PUBLICATIONS

Xin Xie et al., "HCl absorption by CaO/Ca3Al2O6 sorbent from CO2 capture cycles using calcium looping". Fuel Processing Technology, v. 138, p. 500-508. (Year: 2015).*

(Continued)

*Primary Examiner* — Patricia L. Hailey
(74) *Attorney, Agent, or Firm* — Christopher J. Knors; Moore & Van Allen PLLC

(57) ABSTRACT

The invention relates to a composite oxide comprising CaO stabilised by $Ca_3Al_2O_6$ (C3A), wherein the composite is in the form of particles. The mixed oxide composite is useful as a catalyst in the transesterification of triglycerides, e.g. in the production of biodiesel. Calcium leaching is more hindered in CaO—$Ca_3Al_2O_6$ (2Ca/Al) than in CaO-$Al_2O_3$.

31 Claims, 12 Drawing Sheets

(51) Int. Cl.
*B01J 23/00* (2006.01)
*B01J 35/40* (2024.01)
*B01J 35/56* (2024.01)
*B01J 37/00* (2006.01)
*C11C 3/10* (2006.01)

(52) U.S. Cl.
CPC .......... *B01J 35/56* (2024.01); *B01J 37/0027* (2013.01); *C11C 3/10* (2013.01)

(58) Field of Classification Search
CPC ............... B01J 37/0027; B01J 2220/42; B01J 2523/23; B01J 20/04; B01J 20/28004; B01J 20/28016
USPC .... 502/340, 341, 300, 344; 106/792, 287.17
See application file for complete search history.

(56) References Cited

FOREIGN PATENT DOCUMENTS

| | | | |
|---|---|---|---|
| WO | 2011/005114 A1 | 1/2011 | |
| WO | WO-2011007362 A1 * | 1/2011 | ............ B01J 23/002 |

OTHER PUBLICATIONS

Robert Ianos et al., "Fuel mixture approach for solution combustion synthesis of Ca3Al2O6 powders." Cement and Concrete Research 39, pp. 566-572. (Year: 2009).*
Jie-ying Jing et al., "Self-activation of CaO/Ca3Al2O6 sorbents by thermally pretreated in CO2 atmosphere." Applied Energy 220, pp. 419-425. (Year: 2018).*
Despoina Papargyriou et al., "Investigation of solid base catalysts for biodiesel production from fish oil." Renewable Energy 139, pp. 661-669. (Year: 2019).*
Mingming Zhang et al., "Preparation of CaO—Al2O3 sorbent and CO2 capture performance at high temperature." Fuel 111, pp. 636-642. (Year: 2013).*
Cong Luo et al., "Enhanced cyclic stability of CO2 adsorption capacity of CaO-based sorbents using La2O3 or Ca12Al14O33 as additives." Korean Journal of Chemical Engineering 28 (4), pp. 1042-1104. (Year: 2011).*
Ming-Chien Hsiao et al., "Study of Solid Calcium Diglyceroxide for Biodiesel Production from Waste Cooking Oil Using a High Speed Homogenizer." Energies 12, 3205, pp. 1-11. (Year: 2019).*
Jing, Jie-Ying, et al.; "Enhanced CO2 sorption performance of CaO/Ca3Al2O6 sorbents and its sintering-resistance mechanism," Applied Energy, 2017, pp. 225-233, vol. 199.
Jing, Jie-Ying, et al.; "Improving CO2 sorption performance of CaO/Ca3Al2O6 sorbents by thermally pretreated in CO2 atmosphere," Energy Procedia, 2017, pp. 325-3263, 9th International Conference on Applied Energy, ICAE2017, Aug. 21-24, 2017, Cardiff, UK.
Singh, Veena, et al; "Effect of co-solvent on biodiesel production using calcium aluminium oxide as a reusable catalyst and waste vegetable oil", Fuel, 2017, pp. 360-369, vol. 203, XP085046150.
Chakraborty, Rajat, et al; "Biodiesel Synthesis From Mustard Oil (*Brassica nigra*) Using Calcium Oxide-Calcium Aluminate Catalyst Developed From Duck Eggshell," International Journal of Advanced Scientific Research and Technology, 2012, pp. 242-256, vol. 3, No. 2, XP055656606.
Nayebzadeh, Hamed, et al; "Influence of fuel type on microwave-enhanced fabrication of KOH/Ca12Al14O33 hanocatalyst for biodiesel production via microwave heating," Journal of the Taiwan Institute of Chemical Engineers, 2017, pp. 148-155, vol. 75, XP085023322.
Yi, H. C., et al; "Preparation of calcium aluminate matrix composites by combustion synthesis," Journal of Materials Science, 2002, pp. 4537-4543, vol. 37, No. 21, XP001130385.
Madhu, Devarapaga, et al; "Synthesis of High-Quality Biodiesel Using Feedstock and Catalyst Derived from Fish Wastes", Journal of Agricultural and Food Chemistry, 2017, pp. 2100-2109, vol. 65, No. 10, XP055655733.
UKIPO, Search Report for GB Patent Application No. GB1816773.4 dated Apr. 16, 2019, 4 Pages.
European Patent Office; International Search Report and Written Opinion for International Application No. PCT/GB2019/052921 dated Jan. 23, 2020, 20 Pages.
Lee, Adam F., et al.; "Heterogeneous catalysis for sustainable biodiesel production via esterification and transesterification," Chemical Society Reviews, 2014, pp. 7887-7916, vol. 43.
Kesic, Zeljka, et al.; "Calcium Oxide Based Catalysts for Biodiesel Production: A Review," Chemical Industry & Chemical Engineering Quarterly, 2016, pp. 391-408, vol. 22, No. 4.
Oueda, Nombamba, et al.; "Deactivation Processes, Regeneration Conditions and Reusability Performance of CaO or MgO Based Catalysts Used for Biodiesel Production—A Review," Materials Sciences and Applications, 2017, pp. 94-122, vol. 8.
International Bureau of WIPO; International Preliminary Report on Patentability for International Patent Application No. PCT/GB2019/052921 dated Apr. 29, 2021, 10 Pages.
Knothe, Gerhard; "Monitoring a Progressing Transesterification Reaction by Fiber-Optic Near Infrared Spectroscopy with Correlation to 1H Nuclear Magnetic Resonance Spectroscopy," Journal of the American Oil Chemists' Society, 2000, pp. 489-493, vol. 77.
Chouhan, A.P. Singh, et al.; "Modern heterogeneous catalysts for biodiesel production: A comprehensive review," Renewable and Sustainable Energy Reviews, 2011, pp. 4378-4399, vol. 15.
Kim, Manhoe, et al.; "The effect of support material on the transesterification activity of CaO—La2O3 and CaO—CeO2 supported catalysts," Green Chemistry, 2011, pp. 334-339, vol. 13.
Kouzu, Masato, et al.; "Active phase of calcium oxide used as solid base catalyst for transesterification of soybean oil with refluxing methanol," Applied Catalysis A: General, 2008, pp. 357-365, vol. 334.

* cited by examiner

MIXED OXIDE COMPOSITE COMPRISING CALCIUM OXIDE AND TRICALCIUM ALUMINATE

CROSS-REFERENCE TO RELATED APPLICATIONS

This application is a 35 U.S.C. § 371 National Stage Application of International Application No. PCT/GB2019/052921, filed Oct. 14, 2019, which claims priority to GB Application No. 1816773.4 filed on Oct. 15, 2018, the entirety of each of which is incorporated herein by reference.

FIELD OF THE INVENTION

The invention relates to a mixed oxide particulate composite comprising CaO and $Ca_3Al_2O_6$ and a method for preparing same. The mixed oxide particulate composite of the invention is particularly effective as a catalyst in the transesterification of triglycerides, e.g. in the production of biodiesel.

BACKGROUND OF THE INVENTION

Biodiesel is a biodegradable fuel that is produced from plant- or animal-derived oils or fats. Biodiesel can be used as a component of diesel fuel or as a replacement for diesel fuel. Biodiesel is biodegradable, non-toxic and is a cleaner-burning fuel than diesel. Therefore its use can result in substantial environmental benefits.

Biodiesel is comprised of fatty acid methyl esters (FAME) (and also fatty acid ethyl esters) and is obtained from vegetable oils and animal fats. It is produced via the transesterification of triglycerides (TGs) and esterification of free fatty acids (FAAs), the two main components of oil, with alcohols of low molecular weight in the presence of an alkaline catalyst (Lee, A. F., Bennett, J. A., Manayil, J. C., & Wilson, K. (2014). Heterogeneous catalysis for sustainable biodiesel production via esterification and transesterification. *Chem. Soc. Rev.*, 43(22), 7887-7916. https://doi.org/10.1039/C4CS00189C). Homogeneous alkaline catalysts have been widely used for this purpose. However, the use of homogeneous catalysts leads to contamination of the biodiesel and requires separation and purification processes that are very energy intensive, increase the cost of the process and can produce large amounts of wastewater. The use of solid base heterogeneous catalysts for biodiesel production can overcome these issues and improve the process efficiency. More specifically, the catalyst can be easily separated and recycled, making the process more economically feasible and more environmentally friendly. In addition, the separation of the glycerol from the biodiesel is much simpler and no purification step is required (Chouhan, A. P. S., & Sarma, A. K. (2011), Modern heterogeneous catalysts for biodiesel production: A comprehensive review. *Renewable and Sustainable Energy Reviews*, 15(9), 4378-4399. https://doi.org/10.1016/j.rser.2011.07.112). Some of the most promising heterogeneous catalysts for biodiesel production from vegetable oils or animal fats are CaO-based materials (Kesic, Z., Lukic, I., Zdujic, M., Mojovic, L., & Skala, D. (2016). Calcium oxide based catalysts for biodiesel production: A review. *Chemical Industry and Chemical Engineering Quarterly*, 22(4), 391-408. https://doi.org/10.2298/CICEQ160203010K). Deactivation Processes, Regeneration Conditions and Reusability Performance of CaO or MgO Based Catalysts Used for Biodiesel Production—A Review. *Materials Sciences and Applications*, 08(01), 94-122. https://doi.org/10.4236/msa.2017.81007). These catalysts are low-cost materials, with high basicity and demonstrate high activity in moderate reaction conditions, producing high quality biodiesel. However, one of the main limitations of these catalysts is their low stability and deactivation during repeated cycles, due to leaching of CaO (Oueda, N., Bonzi-Coulibaly, Y. L., & Ouédraogo, I. W. K. (2017). Deactivation Processes, Regeneration Conditions and Reusability Performance of CaO or MgO Based Catalysts Used for Biodiesel Production—A Review. *Materials Sciences and Applications*, 08(01), 94-122. https://doi.org/10.4236/msa.2017.81007)(Oueda, Bonzi-Coulibaly, & Ouédraogo, 2017). The effect of some support materials on the transesterification activity of CaO—$La_2O_3$ and CaO—$CeO_2$ has been investigated (Kim, M., DiMaggio, C., Yan, S., Salley, S. O., & Ng, K. Y. S. (2011). The effect of support material on the transesterification activity of CaO—$La_2 O_3$ and CaO—$CeO_2$ supported catalysts. *Green Chem.*, 13(2), 334-339. https://doi.org/10.1039/C0GC00828A).

The aquaculture industry produces large amounts of waste, which has no significant commercial value. A typical example is the farming and processing of tilapia, which is the second most cultivated freshwater fish worldwide. During the food processing, the main product is the fillet of the fish, which represents only 30% of the wet fish weight with the rest discarded. This waste has been typically used in animal feed. However, there is a significant opportunity to utilise this fish waste for renewable fuel. More specifically, as the waste from tilapia processing has high oil content, it is possible to use it as feedstock for biodiesel. Fish oil extracted from waste not only reduces the amount of waste that is generated, but also reduces the total cost of biodiesel synthesis. Moreover, this biodiesel can be used by the local farmers in diesel generators, allowing them to be energy independent, while reducing their waste disposal burden. Therefore, there is a need to provide a low cost, efficient way to produce biodiesel from fish waste.

It is an object of the invention to provide a new catalyst for use in the transesterification of fatty acid glycerol esters and in producing biodiesel. It is an object of the invention to provide a new method for transesterifying fatty acid glycerol esters and for producing biodiesel. In particular, it is an object of the invention to provide such a catalyst and/or a method that alleviates or mitigates at least one of the above-mentioned problems.

SUMMARY OF THE INVENTION

According to a first aspect, the invention provides a mixed oxide composite comprising CaO and $Ca_3Al_2O_6$, wherein the mixed oxide composite is in the form of particles. The composite of the invention comprises two oxide phases, namely a calcium oxide phase (CaO) and a tricalcium aluminate or dialuminium tricacicium hexaoxide phase ($Ca_3Al_2O_6$). The composite is a solid and can act as a heterogeneous catalyst for transesterification of glycerides (mono-, di- and tri-glycerides). It has been found that, for such a reaction: the mixed oxide composite of the invention can be reused; its use results in reduction in the amount of impurities in downstream products when compared to a homogeneous catalyst; it can be further activated in situ (by a side reaction that takes place when CaO reacts with glycerol produced by the transesterification reaction; and it is relatively inexpensive to produce. Furthermore, it has advantages over known heterogeneous transesterification catalysts in that it is more stable (more resistant to CaO leaching and thus has a longer lifetime) and also has a high conversion rate. In particular, it has been found that the Ca$_3$Al$_2$O$_6$ used with the CaO in the composite of the invention enhances the stability of the CaO catalyst during repeated cycling of the transesterification of triglycerides reaction. It is believed that the Ca$_3$Al$_2$O$_6$ enhances the stability of the CaO catalyst in an activated form (calcium diglyceroxide), which activated form is very active for transesterification of glycerides and is formed during the transesterification of glycerides reaction.

According to a second aspect, the invention provides a method for preparing a mixed oxide composite comprising CaO and Ca$_3$Al$_2$O$_6$, wherein the mixed oxide composite is in the form of particles, said method comprising:
(a) heating an aqueous solution comprising calcium and aluminium nitrates or nitrate hydrates and an organic fuel until it combusts to form a powder; and
(b) calcining the powder at a temperature of 1000° C. or higher.

This is a combustion method by which the aqueous solution is heated until it ignites and burns leaving a solid powder residue. The method results in a composite material which comprises a mixture of a CaO phase and a Ca$_3$Al$_2$O$_6$ phase and is in the form of particles. The method of the second aspect of the invention can be used to prepare the mixed oxide composite of the first aspect of the invention. The invention extends to a mixed oxide composite obtainable/obtained by a method according to the second aspect of the invention.

According to a third aspect, the invention provides a method of activating a CaO catalyst comprising heating a C1 to C4 alcohol with glycerol in the presence of the catalyst so as to form calcium diglyceroxide, i.e. so that the CaO reacts with the glycerol to form calcium diglyceroxide. Calcium diglyceroxide has been found to be particularly effective in catalysing the transesterification of fatty acid glycerides with a C1 to C4 alcohol. In this aspect of the invention the CaO catalyst can be a mixed oxide composite according to the first aspect of the invention or a mixed oxide composite obtainable/obtained by a method according to the second aspect of the invention. It is believed that the presence of the Ca$_3$Al$_2$O$_6$ in the composite results in an enhancement of the stability of the CaO in this activated form, i.e. calcium diglyceroxide. The invention extends to an activated CaO catalyst, e.g. an activated mixed oxide composite obtainable/obtained by a method according to the third aspect of the invention. Such an activated catalyst is formed during the transestrifcation of fatty acid monoglycerides, diglycerides or triglycerides with a C1 to C4 alcohol in the presence of a mixed oxide composite of the first aspect of the invention (glycerol is a byproduct of this reaction). CaO in the composite is activated during the transesterification reaction by the formation of an intermediate stable phase of calcium diglycerol oxide.

According to a fourth aspect, the invention provides a method for producing fatty acid alkyl esters comprising reacting a feedstock comprising fatty acid monoglycerides, diglycerides or triglycerides with a C1 to C4 alcohol in the presence of a mixed oxide composite comprising CaO and Ca$_3$Al$_2$O$_6$, wherein the mixed oxide composite is in the form of particles. The method of the invention involves transesterifying the fatty acid monoglycerides, diglycerides or triglycerides with the C1 to C4 alcohol. The transesterification produces fatty acid alkyl esters, including fatty acid methyl esters and fatty acid ethyl esters which are useful as biodiesel. The mixed oxide composite is the mixed oxide composite of the first aspect of the invention or a mixed oxide composite obtainable/obtained by the method of the second aspect of the invention or an activated mixed oxide composite according to the third aspect of the invention.

According to a fifth aspect, the invention provides for the use of a mixed oxide composite comprising CaO and Ca$_3$Al$_2$O$_6$, wherein the mixed oxide composite is in the form of particles, as a catalyst for the transesterification of monoglycerides, diglycerides or triglycerides with a C1 to C4 alcohol. The mixed oxide composite is the mixed oxide composite of the first aspect of the invention or a mixed oxide composite obtainable/obtained by the method of the second aspect of the invention or an activated mixed oxide composite according to the third aspect of the invention. The transesterification of monoglycerides, diglycerides or triglycerides with a C1-C4 alcohol can be according to the method of the fourth aspect of the invention.

BRIEF DESCRIPTION OF THE DRAWINGS

FIG. 5 (b) shows the triglycerides conversion to biodiesel and catalyst reusability during the transesterification reaction of cod liver oil with methanol using the 6Ca/Al composite as a catalyst.

FIG. 5 (c) shows the triglycerides conversion to biodiesel and catalyst reusability during the transesterification reaction of cod liver oil with methanol using the CaO powder as a catalyst.

FIG. 7 (b) shows the SEM micrograph of the as-prepared 3Ca/Al composite.

FIG. 7 (c) shows the SEM micrograph of the as-prepared 2Ca/Al composite.

FIG. 7 (d) shows the SEM micrograph of the as-prepared C3A.

DETAILED DESCRIPTION OF THE INVENTION

Figure 1A:
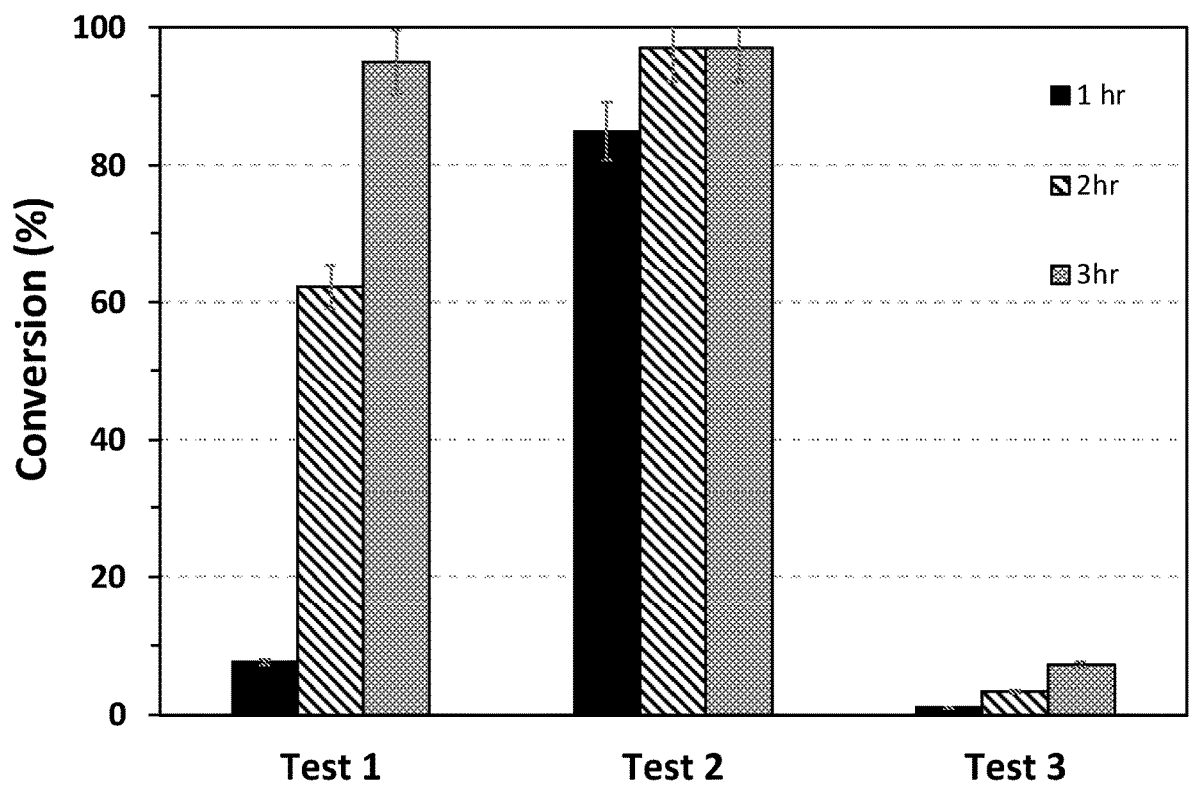
FIG. 1(a) shows biodiesel yield and catalyst reusability during the transesterification reaction of cod liver oil with methanol using CaO—Al$_2$O$_3$ as a catalyst.

In a first aspect, the invention provides a mixed oxide composite comprising CaO and $Ca_3Al_2O_6$, wherein the composite is in the form of particles. The composite of the invention comprises a mixture of two oxide phases, namely a calcium oxide phase (CaO) and a tricalcium aluminate phase ($Ca_3Al_2O_6$). A particle of the composite of the invention comprises a mixture of two oxide phases, namely a calcium oxide phase (CaO) and a tricalcium aluminate phase ($Ca_3Al_2O_6$). The mixed oxide composite of the invention is also referred to herein as a composite, a particulate composite, a mixed oxide composite or a mixed oxide particulate composite.

The mixed oxide composite comprises CaO and $Ca_3Al_2O_6$ but may also comprise other oxides such as silicates, strontium oxide, magnesium oxide, and may also comprise calcium sulphate. Preferably, the mixed oxide composite comprises CaO and $Ca_3Al_2O_6$ as a major component, i.e. the amount of CaO and $Ca_3Al_2O_6$ in the composite represents greater than 50 wt % based on the total weight of the composite and the amount of any other component is less than 50 wt %. By the amount of CaO and $Ca_3Al_2O_6$ is meant the total of the amount of CaO and the amount of $Ca_3Al_2O_6$. The amount of CaO and $Ca_3Al_2O_6$ in the composite can represent greater than 60, 70, 80, 90, 95, 98 or 100 wt % based on the total weight of the composite. In a preferred embodiment, the amount of CaO and $Ca_3Al_2O_6$ in the composite represents 100 wt % based on the total weight of the composite. In a preferred embodiment, the composite of the invention is biphasic with respect to oxide phases, i.e. the mixed oxide composite contains no oxide phases other than a CaO phase and a $Ca_3Al_2O_6$ phase. This is a composite is referred to herein as a CaO—$Ca_3Al_2O_6$ composite. This embodiment includes a composite where the amount of CaO and $Ca_3Al_2O_6$ in the composite represents 100 wt % of the composite. In another embodiment, the CaO—$Ca_3Al_2O_6$ composite can consist essentially of CaO and $Ca_3Al_2O_6$.

The amount of CaO and $Ca_3Al_2O_6$ in the composite based on the total weight of the composite can be determined by means known in the art, for example X-ray diffraction analysis using standards and chemical analysis.

The relative amounts of calcium oxide and tricalcium aluminate in the composite can vary. The percentage weight of CaO based on the total weight of CaO and $Ca_3Al_2O_6$ can range from 10 to 75 wt % (thus the percentage weight of $Ca_3Al_2O_6$ based on the total weight of CaO and $Ca_3Al_2O_6$ ranges from 90 to 25 wt %). Thus the invention provides a mixed oxide composite comprising CaO and $Ca_3Al_2O_6$, wherein CaO is present in an amount of 10 to 75 wt % based on the total weight of CaO and $Ca_3Al_2O_6$ and, wherein the composite is in the form of particles. The percentage weight of CaO based on the total weight of CaO and $Ca_3Al_2O_6$ can range from 15 to 75 wt %. The percentage weight of CaO based on the total weight of CaO and $Ca_3Al_2O_6$ can range from 25 to 75 wt %. The percentage weight of CaO based on the total weight of CaO and $Ca_3Al_2O_6$ can range from 35 to 70 wt %. The percentage weight of CaO based on the total weight of CaO and $Ca_3Al_2O_6$ can range from 55 to 70 wt %. The percentage weight of CaO based on the total weight of CaO and $Ca_3Al_2O_6$ can be 38 wt %, i.e. the molar ratio of Ca to Al in the composite is 3. The percentage weight of CaO based on the total weight of CaO and $Ca_3Al_2O_6$ can be 65 wt %, i.e. the molar ratio of Ca to Al in the composite is 6. Where the amount of CaO and $Ca_3Al_2O_6$ in the composite represents 100 wt % of the composite and the percentage weight of CaO is greater than about 80 wt %, composite stability issues may arise.

The relative amounts of calcium oxide and tricalcium aluminate in the composite can vary as described above for each embodiment of the composite as described herein. This includes embodiments where the composite comprises other components, for example, where the amount of CaO and $Ca_3Al_2O_6$ in the composite represents greater than 50, 60, 70, 80, 90, 95, 98 or 100 wt % based on the total weight of the composite.

The percentage weights of CaO and $Ca_3Al_2O_6$ relative to the total amount of CaO and $Ca_3Al_2O_6$ present can be determined using techniques known in the art such as inductively coupled plasma optical emission spectroscopy (ICP-OES).

The composite particles can have an average size of from 10 nm to 100 μm, and preferably they have a size of 100 nm to 1000 nm, 500 to 1000 nm or 100 to 500 nm. By size of a particle is meant the size of the longest dimension (also referred to herein as the longest diameter) of the particle as measured from an SEM micrograph.

Preferably the particles of the mixed oxide composite comprise a uniformly dispersed mixture of CaO and $Ca_3Al_2O_6$. This is indicated by a more uniform and smaller particle size in SEM images of the composite and is more typical of composite particles of the invention that have high weight percentages (e.g. greater than 35 wt %, when the amount of CaO and $Ca_3Al_2O_6$ in the composite represents 100 wt % of the composite) of the CaO. The particles can be partially coated with CaO coated on $Ca_3Al_2O_6$ support. This is more typical of composite particles of the invention that have lower weight percentage of CaO.

The presence of the CaO and $Ca_3Al_2O_6$ phases can be determined by routine XRD analysis and EDX (Energy Dispersive X-Ray Spectroscopy) analysis, for example.

The mixed oxide composite of the invention has been found to be particularly effective in catalysing the transesterification of triglycerides with lower alcohols in the formation of acid alkyl esters which are useful in biodiesel production. One of the advantages is that as the composite is solid, it is a heterogeneous catalyst for this reaction and, as such, easier to separate from a reaction mixture than a homogeneous catalyst.

The mixed oxide composite of the invention, which is in the form of particles, can be supported on a support, such as a monolith. Suitable monoliths are well known in the art and include corderite and alumina. The mixed oxide composite can be coated on a porous support such as a monolith using deep coating techniques known in the art. The mixed oxide composite of the invention can also be self-supporting, i.e. the composite particles can be moulded into the form of a self-supporting structure. For example, the composite particles can be pressed into a mould to form a self-supporting structure. Ceramic injection moulding techniques known in the art can be used. The self-supporting structure can be a honeycomb structure, for example. In both cases, the catalyst is rendered easier to remove from the reaction mixture once the reaction has completed.

In a second aspect, the invention provides a method for preparing a mixed oxide composite comprising CaO and $Ca_3Al_2O_6$, wherein the composite is in the form of particles, said method comprising:

(a) heating an aqueous solution comprising (i) calcium nitrate or calcium nitrate hydrate, (ii) aluminium nitrate or aluminium nitrate hydrate, and (iii) an organic fuel until the solution combusts to form a powder; and (b) calcining the powder at a temperature of from 1000° C. or higher.

The aqueous solution can also contain nitrates or nitrate hydrates of other elements such as silica, magnesium or strontium. These other nitrates or nitrate hydrates are optional. The method of the second aspect of the invention can be used to prepare the mixed metal oxide composite of each of the above-described embodiments of the first aspect of the invention.

The aqueous solution contains calcium nitrate or calcium nitrate hydrate and aluminium nitrate or aluminium nitrate hydrate, i.e. it contains calcium in the form of a nitrate or a nitrate hydrate and aluminium in the form of a nitrate or a nitrate hydrate. For example, the aqueous solution can contain $Ca(NO_3)_2$ or $Ca(NO_3)_2 \cdot 4H_2O$ and $Al(NO_3)_2$ or $Al(NO_3)_2 \cdot 9H_2O$. Preferably, the aqueous solution contains $Ca(NO_3)_2 \cdot 4H_2O$ and $Al(NO_3)_2 \cdot 9H_2O$. By varying the relative amounts of calcium and aluminium nitrates (or nitrate hydrates) used in the reaction mixture, the relative quantities of CaO and $Ca_3Al_2O_6$ in the resultant composite particles can be altered. The relative amounts of calcium and aluminium nitrates (or nitrate hydrates) used can be such that so that a composite having a percentage weight of CaO based on the total weight of CaO and $Ca_3Al_2O_6$ in the range from 10 to 75 wt %, 15 to 75 wt %, 25 to 75 wt %, 35 to 70 wt %, 55 to 70 wt % or of 38 wt % or of 65 wt % is obtained.

The aqueous solution also contains an organic fuel to aid combustion. The organic fuel can be, for example, ethylene glycol, citric acid, urea, glycine, sucrose or mixtures thereof. A preferred organic fuel is a mixture of ethylene glycol and citric acid.

The aqueous solution contains water and, preferably, contains deionised water.

The combustion involves an exothermic reaction of the metal nitrates (or metal nitrate hydrates) and the organic fuel. Upon sufficient heating, the mixture foams and ignites with the evolution of gases and the resultant product crumbles into a powder. Preferably the solution is heated to temperatures of from 250 to 500° C. to cause combustion.

Step (a) of the method of the second aspect of the invention can involve heating the aqueous solution containing calcium and aluminium nitrates or nitrate hydrates, optional other nitrates and nitrate hydrates, and an organic fuel to evaporate water so as to form a gel, followed by further heating of the gel until it combusts to form a powder. For example, step (a) can involve heating the aqueous solution containing calcium and aluminium nitrates or nitrate hydrates, optional other nitrates and nitrate hydrates, and an organic fuel to a temperature of 100° C. to evaporate water so as to form a gel, followed by further heating of the gel to a temperature of from 250 to 500° C. or of about 300° C. until it combusts to form a powder. Combustion involves the gel igniting and burning, leaving a powder residue.

Step (a) of the method of the second aspect of the invention can involve heating the aqueous solution containing calcium and aluminium nitrates or nitrate hydrates, and an organic fuel to evaporate water so as to form a gel, followed by further heating of the gel until it combusts to form a powder. For example, step (a) can involve heating the aqueous solution containing calcium and aluminium nitrates or nitrate hydrates, optional other nitrates and nitrate hydrates, and an organic fuel to a temperature of 100° C. to evaporate water so as to form a gel, followed by further heating of the gel to a temperature of from 250 to 500° C. or of about 300° C. until it combusts to form a powder. Combustion involves the gel igniting and burning, leaving a powder residue.

In step (b) of the method of the second aspect of the invention, the powder resulting from the combustion is calcined at a temperature of 1000° C. or higher, or from 1000 to 1542° C. or from 1000 to 1250 or 1300° C. The object of the calcination step is to decompose the nitrates to oxides and, e.g. form the $Ca_3Al_2O_6$ structure via a solid state reaction between CaO and $Al_2O_3$. Typically, the powder is calcined for 2 to 12 hours, and can be calcined for about 5 hours, for example. The product of the calcination step (b) is a mixed oxide composite comprising CaO and $Ca_3Al_2O_6$, wherein the composite is in the form of particles.

The method of the second aspect of the invention can comprise a method for preparing a mixed oxide composite comprising CaO and $Ca_3Al_2O_6$, wherein the mixed oxide composite is in the form of particles, said method comprising:

(a) heating an aqueous solution of (i) calcium nitrate or calcium nitrate hydrate, (ii) aluminium nitrate or aluminium nitrate hydrate, and (iii) an organic fuel until the solution combusts to form a powder; and (b) calcining the powder at a temperature of from 1000° C. or higher.

In this embodiment, the method results in a composite material which is a mixture of a CaO phase and a $Ca_3Al_2O_6$ phase and is in the form of particles. That is the composite is biphasic with respect to oxide phases, i.e. the mixed oxide composite contains no oxide phases other than a CaO phase and a $Ca_3Al_2O_6$ phase. This embodiment of the method of the invention can be used to prepare a composite in which the amount of CaO and $Ca_3Al_2O_6$ in the composite represents 100 wt % of the composite.

The method of the second aspect of the invention can comprise:

(a) (i) adding $Ca(NO_3)_2 \cdot 4H_2O$ and $Al(NO_3)_2 \cdot 9H_2O$ to a solution of deionised water, ethylene glycol and citric acid;

(ii) heating the solution under stirring at a temperature of 100° C. to evaporate the water and thereby form a gel;

(iii) combusting the gel at a temperature of 250 to 500 or 300° C. to form a powder; and (b) calcining the powder at a temperature of from 1000 to 1250° C. for from 5 to 12 hours.

The method of the second aspect of the invention can comprise:

(a) (i) adding $Ca(NO_3)_2 \cdot 4H_2O$ and $Al(NO_3)_2 \cdot 9H_2O$ to a solution of deionised water, ethylene glycol and citric acid;

(ii) heating the solution under stirring at a temperature of 100° C. to evaporate the water and thereby form a gel;

(iii) combusting the gel at a temperature of 300° C. to form a powder; and (b) calcining the powder at a temperature of 1000 for 5 hours.

The invention also provides for a mixed oxide composite obtainable or obtained by the method of the second aspect of the invention, in each of its embodiments.

For example, the invention extends to a mixed oxide composite obtainable or obtained by a method for preparing a mixed oxide composite comprising CaO and $Ca_3Al_2O_6$, wherein the mixed oxide composite is in the form of particles, which method comprises:

(a) (i) adding $Ca(NO_3)_2 \cdot 4H_2O$ and $Al(NO_3)_2 \cdot 9H_2O$ to a solution of deionised water with ethylene glycol and citric acid added;

(ii) heating the solution under stirring at a temperature of 100° C. to evaporate the water and thereby form a gel;

(iii) combusting the gel at a temperature of 250 to 500 or 300° C. to form a powder; and (b) calcining the powder at a temperature of from 1000 to 1250° C. for 5 to 12 hours.

According to a third aspect, the invention provides a method of activating a CaO catalyst comprising heating a C1 to C4 alcohol, preferably methanol, with glycerol in the presence of the catalyst so as to form calcium diglyceroxide. The calcium oxide reacts with the glycerol to form calcium diglyceroxide. Calcium diglyceroxide has been found to be particularly effective in catalysing the transesterification of fatty acid glycerides with a C1 to C4 alcohol. In this aspect of the invention the CaO catalyst can be a mixed oxide composite according to the first aspect of the invention or a mixed oxide composite obtainable/obtained by a method according to the second aspect of the invention. The invention extends to an activated CaO catalyst, e.g. an activated mixed oxide composite obtainable/obtained by a method according to the third aspect of the invention. The activated CaO catalyst (i.e. calcium diglyceroxide-containing catalyst) is formed during the transestrifcation of fatty acid monoglycerides, diglycerides or triglycerides with a C1 to C4 alcohol in the presence of a mixed oxide composite of the first aspect of the invention (glycerol is a byproduct of this reaction). This reaction is discussed below in relation to the fourth aspect of the invention, and similar reaction conditions apply. For example, the reaction mixture is heated to a temperature that does not exceed the boiling point of the alcohol. The reaction is usually carried out at atmospheric pressure and at a temperature of below 65° C., preferably at from 50 to 65° C. 65° C. is the boiling point of methanol at atmospheric pressure. The reaction can also be performed at higher temperatures under pressure higher that atmospheric pressure, provided the alcohol remains in the liquid state. Further, preferably the alcohol is methanol or ethanol. More preferably the alcohol is methanol.

According to a fourth aspect, the invention provides a method for producing fatty acid alkyl esters comprising reacting a feedstock comprising fatty acid monoglycerides, diglycerides or triglycerides with a C1 to C4 alcohol in the presence of a mixed oxide composite comprising CaO and $Ca_3Al_2O_6$, wherein the mixed composite is in the form of particles. The method of the invention involves transesterifying the fatty acid monoglycerides, diglycerides or triglycerides with the C1 to C4 alcohol. The transesterification produces fatty acid alkyl esters, including fatty acid methyl esters and fatty acid ethyl esters which are particularly useful as biodiesel. The mixed oxide composite is the mixed oxide composite of the first aspect of the invention or a mixed oxide composite obtainable/obtained by the method of the second aspect of the invention or an activated mixed oxide composite according to the third aspect of the invention.

The feedstock can be a plant oil and/or an animal oil or fat. For example, the feedstock can be a vegetable oil (e.g. rape seed oil or palm oil), tallow or an oil derived from an animal (e.g. a fish). Suitable fish oils include cod liver oil and oil derived from tilapia. Preferably the oil is high in triglycerides. The oil or fat can treated with glycerol to convert free fatty acids to triglycerides thus lowering the free fatty acid content of the plant oil/animal oil/animal fat feedstock.

The method of the invention involves transesterifying the fatty acid monoglycerides, diglycerides or triglycerides with the C1 to C4 alcohol. Transesterification of triglycerides with an alcohol proceeds in a reversible equilibrium reaction according to the scheme:

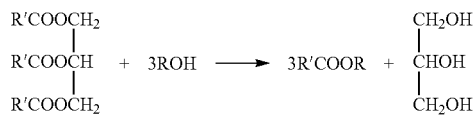

In the above formulae, R' represent the hydrocarbyl moieties of fatty acid constituents of the vegetable oils and R is a C1-C4 alkyl group. As shown in the above scheme, glycerol is formed as a byproduct in addition to the fatty acid alkyl esters usable as fuel. The equilibrium can be shifted towards the formation of the required fatty acid esters by increasing the amount of alcohol reactant and/or by removing the glycerol byproduct.

Typically the feedstock is reacted with the alcohol in the presence of the catalyst at a temperature below the boiling point of the alcohol. The reaction mixture comprises feedstock (fatty acid glycerides), alcohol and catalyst. These components are added to a reaction vessel and the reaction mixture is heated to a temperature that does not exceed the boiling point of the alcohol. The reaction is usually carried out at atmospheric pressure and at a temperature of below 65° C., preferably at from 50 to 65° C. 65° C. is the boiling point of methanol at atmospheric pressure. The reaction can also be performed at higher temperatures under pressure higher that atmospheric pressure, provided the alcohol remains in the liquid state. The use of higher temperature increases the reaction rate. As the alcohol and the feedstock have limited miscibility in each other, preferably the reaction mixture is stirred. Glycerol, which is generated as a by-product, accumulates in the polar (alcohol) phase of the reaction mixture and, in accordance with the equilibrium nature of the reaction, is prone to reconvert the produced fatty acid alkyl esters into glyceride esters. Thus full conversion of the vegetable oil cannot be attained. After a period, the reaction mixture is taken off heat and the catalyst is recovered from the reaction mixture. The reaction mixture can be filtered to remove (separate out) the catalyst. Prior to filtering, the reaction mixture can be centrifuged, after which the liquid (containing the desired fatty acid alkyl esters) is decanted off leaving a portion of the reaction mixture containing the catalyst. This remaining portion of the reaction mixture containing the catalyst is filtered, preferably under vacuum, to remove the catalyst. If the catalyst is still active, e.g. if it has not been deactivated due to extended use in transesterification, it can be reused. Preferably it is washed and dries before reuse. It can be washed in methanol and dried, for example in an oven at 80° C. for about 12 hours, prior to reuse. The decanted liquid containing the fatty acid alkyl esters is allowed to stand for a period of time without stirring to allow it to separate into two phases. The lower polar phase which contains alcohol and glycerol is removed, leaving the upper apolar phase (fuel phase) which contains the fatty acid alkyl esters. This upper apolar phase can be further refined, for example, by being subjected to distillation to remove any methanol that may be present.

The amount of alcohol used is the amount effective to undergo the transesterification with the feedstock oil in the appropriate stoichiometric ratios. Usually an excess of alcohol is used. The alcohol can be methanol, ethanol, propanol, butanol or mixtures thereof. When the alcohol is methanol, the method produces fatty acid methyl esters, i.e. it is a method for producing biodiesel. When the alcohol is ethanol, the method produces fatty acid ethyl esters, i.e. it is a method for producing biodiesel. Preferably the alcohol is methanol.

Typically the composite is present in an amount of 1 to 40 weight percent based on the weight of the feedstock.

The reaction can take place in a continuous flow reactor in which the feedstock and the alcohol form a feedstream that is continuously flowed over a fixed catalyst bed. This method attracts economies associated with efficiency of process and is particularly suited to the catalyst of the invention due to its high stability. As the catalyst of the invention has high stability (i.e. it takes longer to deactivate than known CaO catalysts), it does not have to be replaced so often and therefore is more suited to use in a continuous flow, fixed bed reactor.

According to a fifth aspect, the invention provides for the use of a mixed oxide composite comprising CaO and $Ca_3Al_2O_6$, wherein the mixed oxide composite is in the form of particles, as a catalyst for the transesterification of monoglycerides, diglycerides or triglycerides with a $C_1$-C alcohol. The mixed oxide composite is the mixed oxide composite of the first aspect of the invention or a mixed oxide composite obtainable/obtained by the method of the second aspect of the invention or an activated mixed oxide composite according to the third aspect of the invention. The transesterification of monoglycerides, diglycerides or triglycerides with a $C_1$-C alcohol can be according to the method of the fourth aspect of the invention.

As used herein, the term "comprising", which is inclusive or open-ended and does not exclude additional unrecited elements or method steps, is intended to encompass as alternative embodiments, the phrases "consisting essentially of" and "consisting of" where "consisting of" excludes any element or step not specified and "consisting essentially of" permits the inclusion of additional unrecited elements or steps that do not materially affect the essential or basic and novel characteristics of the composition or method under consideration.

The advantages of the method of the invention are discussed below in relation to the following non-limiting examples.

EXAMPLES

Synthesis of Catalysts

Six catalysts were prepared.

The first catalyst was synthesized by incipient wetness impregnation of CaO on $Al_2O_3$. The resultant CaO impregnated $Al_2O_3$ catalyst is also referred to herein as CaO—$Al_2O_3$. For the synthesis of this catalyst, $Al_2O_3$ powder was added in ethanol at room temperature under stirring with the stoichiometric amount of $Ca(NO_3)_2 \cdot 4H_2O$, required to obtain 20 wt % of CaO loading on the $Al_2O_3$ support, based on the total weight of CaO and $Al_2O_3$. The solution was left under stirring at 60° C., until the ethanol was evaporated. After calcination at 750° C., the CaO impregnated $Al_2O_3$ (CaO—$Al_2O_3$) catalyst was obtained.

The second catalyst is a mixed oxide phase of CaO and $Ca_3Al_2O_6$ ($Ca_3Al_2O_6$ is also referred to as C3A herein) that was synthesized via combustion. $Ca(NO_3)_2 \cdot 4H_2O$ and $Al(NO_3)_3 \cdot 9H_2O$ were diluted in deionized water, with ethylene glycol and citric acid. The amounts of $Ca(NO_3)_2 \cdot 4H_2O$ and $Al(NO_3)_3 \cdot 9H_2O$ used were so that the molar ratio of Ca:Al was 2. The solution was heated under stirring at 100° C. in order to evaporate the water and form a gel. The gel was then combusted at 300° C. The resulting powder was calcined at 1000° C. for 5 h (hours) and a particulate composite comprising a mixture of CaO and $Ca_3Al_2O_6$ (C3A) phases was obtained. The calculated weight percents of each of the CaO and the C3A phases in the composite based on the total weight of CaO and C3A were 17 wt % of CaO and 83 wt % of C3A. The resultant CaO—$Ca_3Al_2O_6$ composite catalyst is also referred to herein as 2Ca/Al.

The third catalyst was prepared according to the same procedure as the second catalyst except that the amounts of $Ca(NO_3)_2 \cdot 4H_2O$ and $Al(NO_3)_3 \cdot 9H_2O$ used were so that the molar ratio of Ca:Al was 3. The calculated weight percents of each of the CaO and the C3A phases in the composite based on the total weight of CaO and C3A were 38 wt % of CaO and 62 wt % of C3A. The resultant CaO—$Ca_3Al_2O_6$ composite catalyst is also referred to herein as 3Ca/Al.

The fourth catalyst was prepared according to the same procedure as the second catalyst except that the amounts of $Ca(NO_3)_2 \cdot 4H_2O$ and $Al(NO_3)_3 \cdot 9H_2O$ used were so that the molar ratio of Ca:Al was 6. The calculated weight percents of each of the CaO and the C3A phases in the composite based on the total weight of CaO and C3A were 65 wt % of CaO and 35 wt % of C3A. The resultant CaO—$Ca_3Al_2O_6$ composite catalyst is also referred to herein as 6Ca/Al.

The fifth catalyst was prepared according to the same procedure as the second catalyst except that the amounts of $Ca(NO_3)_2 \cdot 4H_2O$ and $Al(NO_3)_3 \cdot 9H_2O$ used were so that the molar ratio of Ca:Al was 1.5. The calculated weight percents of CaO and C3A phase in the composite based on the total weight of CaO and C3A were 0 wt % of CaO and 100 wt % of C3A. The resultant $Ca_3Al_2O_6$ catalyst is also referred to herein as C3A.

The sixth catalyst was a commercially available CaO powder that was calcined at 750 C for 5 hours to remove any impurities such as $Ca(OH)_2$ of $CaCO_3$.

Characterisation of the Catalysts

Room temperature powder X-ray diffraction (XRD) was performed with a PANalytical Empyrean diffractometer operated in reflection mode using Cu-Kα1 radiation. The obtained XRD patterns were analysed with STOE WinXPOW software to determine the crystal structure of the catalysts and the evolution of different phases during testing.

The microstructure of the samples was analysed with a JEOL JSM-5600 scanning electron microscope (SEM). Elemental analysis was performed with an Oxford Inca EDX system.

The Ca/Al ratios, and the weight percents of the CaO and C3A, of the catalysts was determined by inductively coupled plasma optical emission spectroscopy (ICP-OES) on a Thermo-iCAP 6000 spectrometer. The samples were treated in hydrochloric acid and compared to standards.

The total basicity of the prepared catalysts was measured based on their temperature programmed $CO_2$ desorption profiles. The catalysts were pretreated at 800° C. under an Ar flow rate of 50 ml/min to remove any adsorbed $CO_2$ and water from their surface and then cooled down to 50° C. At this temperature, the $CO_2$ chemisorption was carried out by a $CO_2$ flow rate of 50 ml/min for 2 h. The excess of $CO_2$ was then desorbed at the temperature of the adsorption in an Ar flow (50 ml/min) for 2 h. Finally, desorption of $CO_2$ took place with Ar from 50 to 800° C. The evolution of the mass of the catalysts during these treatments was measured by Thermogravimetric analysis (TGA) in a Netzsch STA 449C instrument. The TGA was equipped with a Pfeiffer mass spectrometer (MS), which analysed the $CO_2$ evolution during the different steps.

Transesterification Reaction

Transesterification of cod liver oil was performed in a 100 ml three-neck round bottom flask equipped with a water-cooled reflux condenser and a magnetic stirrer. The temperature was controlled at 65° C. with an oil bath and it was monitored during the reaction with a thermocouple probe that was placed in the reaction mixture. The reaction mixture was stirred at 800 rpm in order to achieve uniform temperature distribution and suspension of the catalyst in the fish oil and methanol mixture. Samples from the reaction mixture were collected at different time intervals, for monitoring the evolution of the transesterification reaction. After running the reaction for the desired duration, the mixture was centrifuged at 1400 rpm, the liquid was decanted, and the remaining catalyst was filtered under vacuum and washed thoroughly with methanol. Then, the recovered catalyst was dried in an oven (80° C.) overnight and was used for analysis and stability tests. No fresh catalyst was added during the stability tests. The reaction was carried out with an oil to methanol ratio of 1 to 12, catalyst loading of 10 wt % based on the fish oil weight and reaction time of maximum 4 h.

The conversion of the fish oil triglycerides to the methyl esters of the biodiesel was determined by $^1H$ Nuclear Magnetic Resonance (NMR) u a Bruker AVII 400 NMR spectrometer. The biodiesel yield was calculated based on the integration of the signal at 3.68 ppm of the hydrogen of the methoxy groups in the methyl esters and the signal at 2.30 ppm of the hydrogen of the methylene groups of the fatty acid derivatives (Knothe, G. (2000). Monitoring a progressing transesterification reaction by fiber-optic near infrared spectroscopy with correlation to 1H nuclear magnetic resonance spectroscopy. *JAOCS, Journal of the American Oil Chemists' Society*, 77(5), 489-493. https://doi.org/10.1007/s11746-000-0078-5).

Experiment 1

Figure 1B:
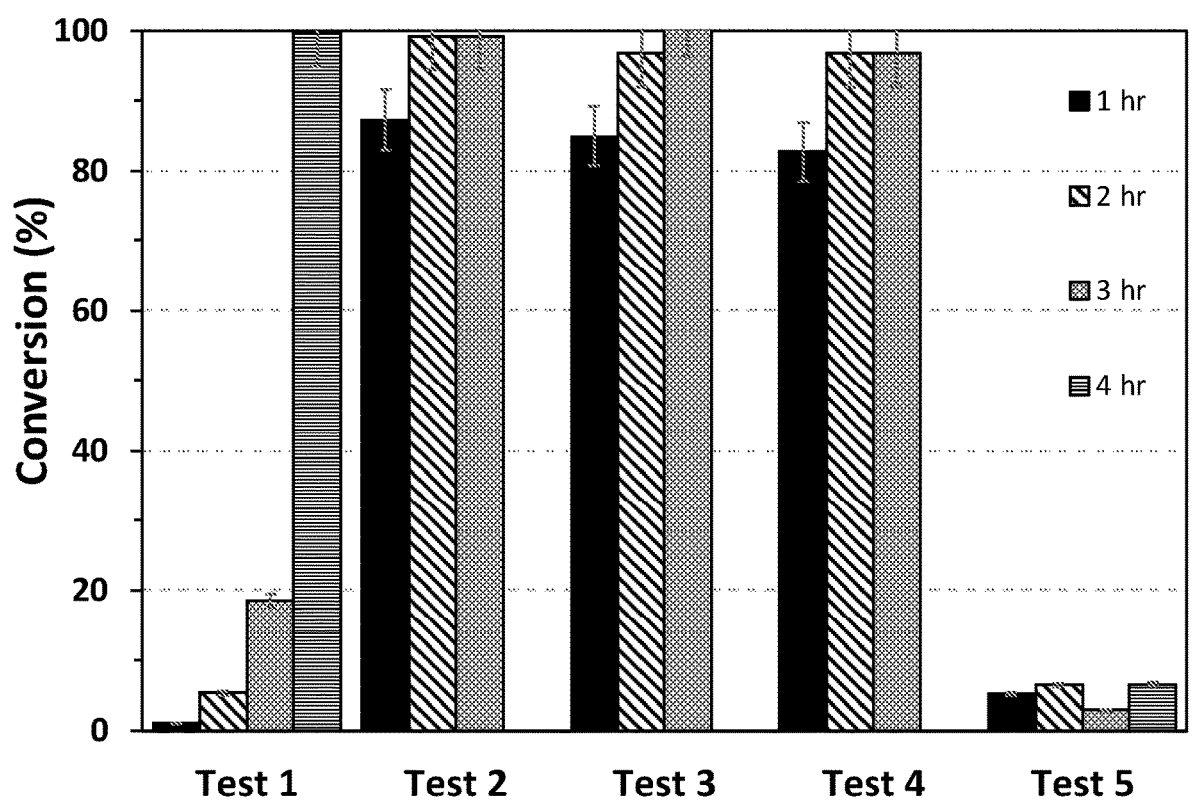
FIG. 1(b) shows biodiesel yield and catalyst reusability during the transesterification reaction of cod liver oil with methanol using the 2Ca/Al composite as a catalyst.

The catalytic activity of each of the first two catalysts ($CaO-Al_2O_3$ and 2Ca/Al) was evaluated based on the biodiesel yield during the transesterification reaction of fish oil triglycerides, operating at the reaction conditions described above. FIG. 1 shows the evolution of the biodiesel yield in hourly time intervals, until the reaction reached over 90% conversion, and the recyclability of the two different catalysts. Comparing the activity of the two materials during the first test, $CaO-Al_2O_3$ demonstrated faster reaction rates than 2Ca/Al. The reaction reached over 90% conversion in 3 hours, while for 2Ca/Al 4 hours reaction time was necessary. However, both catalysts showed faster reaction kinetics when they were reused for test 2 and demonstrated a biodiesel yield of over 90% in 2 hours. During the first hour of test 1, the biodiesel yield was less than 10% for both catalysts. However, in test 2 the biodiesel yield was over 80% during the first hour of reaction for both catalytic systems. These changes in the catalysts activity are attributed to changes in their structure, and this is discussed later.

The recyclability of the catalyst is another important parameter to be considered when designing heterogeneous catalysts for biodiesel production. FIG. 1 presents the recyclability of the two catalysts, when operating at the same conditions. $CaO-Al_2O_3$ catalyst was successfully recycled for 2 tests, but it was fully deactivated by test 3. On the other hand, 2Ca/Al performed with over 90% biodiesel yield for 4 tests, in 2 hours reaction time. This catalyst was fully deactivated by test 5. These results suggest that the 2Ca/Al system was more stable than $CaO-Al_2O_3$ and that the C3A phase improved the stability of the CaO phase and increased the catalyst lifetime.

XRD Analysis

Figure 2A:
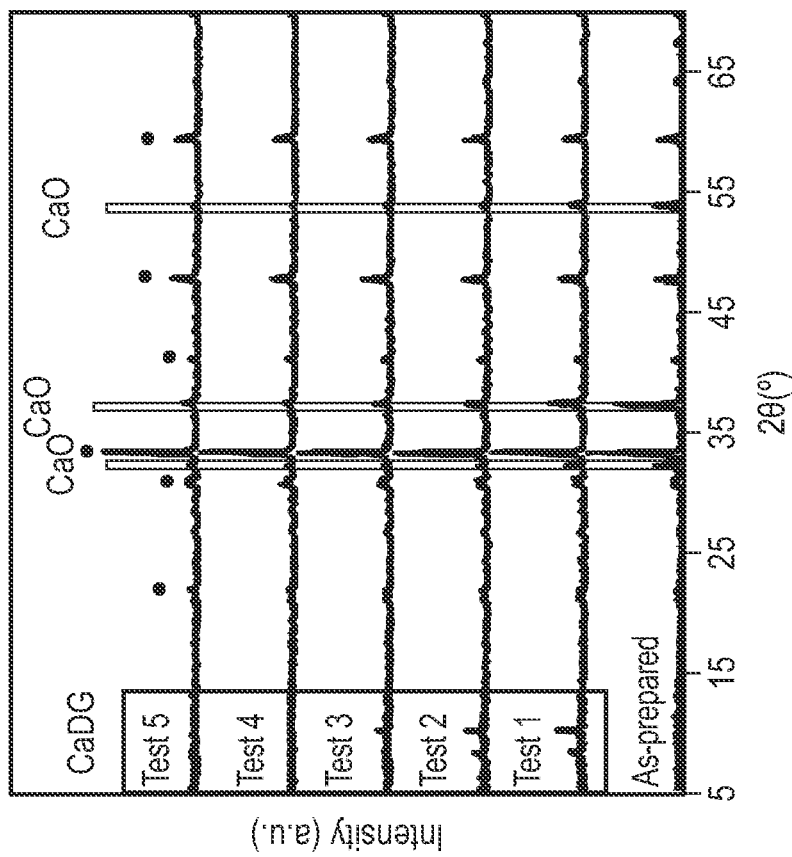
FIG. 2(a) shows evolution of the post-test XRD patterns of the CaO—Al$_2$O$_3$ catalyst (* represents the Al$_2$O$_3$ phase) following the series of biodiesel production tests from cod liver oil of Experiment 1.

In order to explain the changes in the catalysts activity and their deactivation process, the phase evolution of the materials after each test was investigated. According to FIG. 2a, the XRD pattern of the as-prepared $CaO-Al_2O_3$ catalyst shows the peaks that correspond to $Al_2O_3$, which was the support, and CaO, that was impregnated on it. After test 1, the $Al_2O_3$ peaks were still present, but the intensity of the CaO peaks decreased significantly. Moreover, the formation of an extra phase took place, which was calcium diglyceroxide (CaDG). This phase gradually disappeared during test 2 and test 3. Finally, when the catalyst was deactivated, the phases that were mainly present were the $Al_2O_3$ and CaO with decreased intensity, compared to the fresh catalyst.

Figure 2B:
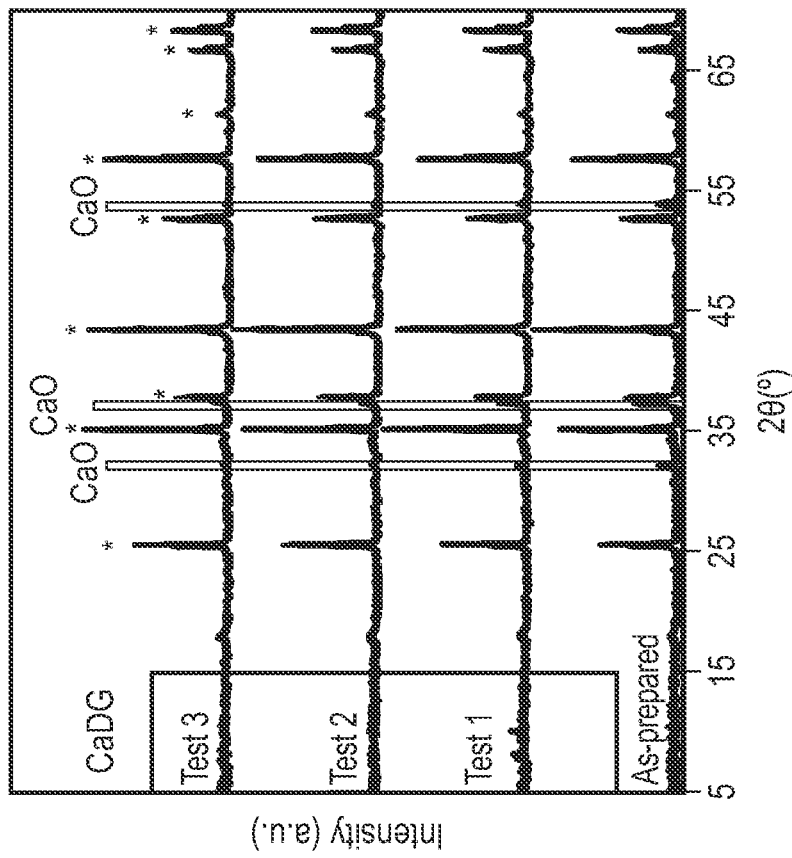
FIG. 2(b) shows evolution of the post-test XRD patterns of the 2Ca/Al composite (• represents the C3A phase—Ca$_3$Al$_2$O$_6$ is also referred to herein as C3A) following the series of biodiesel production tests from cod liver oil of Experiment 1.

FIG. 2b illustrates the evolution of the XRD patterns of the 2Ca/Al catalyst. For the as-prepared catalyst the phases of CaO and C3A are evident with no additional phases. After the first test, the C3A phase was retained, but the CaO phase decreased, while the formation of CaDG took place. The CaDG phase gradually disappeared during the recyclability tests and when the catalyst was deactivated the C3A phase was present with a lower content of CaO.

The formation of the CaDG phase after test 1, that took place for both catalysts, can explain the enhanced catalytic activity of the materials in test 2 onwards. According to the literature, this phase can be formed when CaO reacts with the glycerol by-product of the transesterification reaction. This phase has proved to be more active, due to the presence of a basic non-protonated $O^-$ anion on the surface of CaDG (Kouzu, M., Kasuno, T., Tajika, M., Yamanaka, S., & Hidaka, J. (2008). Active phase of calcium oxide used as solid base catalyst for transesterification of soybean oil with refluxing methanol. *Applied Catalysis A: General*, 334(1-2), 357-365. https://doi.org/10.1016/j.apcata.2007.10.023). Finally, the decreased intensity of the CaO peaks and the gradual disappearance of the CaDG phase suggest possible leaching of Ca ions, which led to the deactivation of the catalyst.

SEM and EDX Analysis

The microstructure of the catalysts was studied by SEM and the elemental analysis was performed with EDX in different areas of the samples. The Ca/Al molar ratios were calculated for the as-prepared and the deactivated catalysts, in order to estimate the extent of Ca leaching for each catalyst.

Figure 3A:
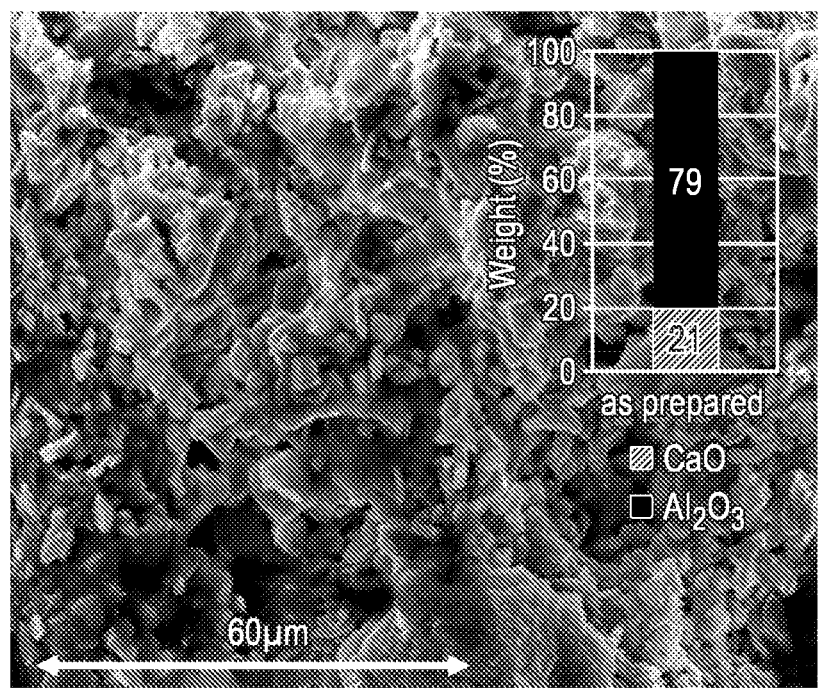
FIG. 3(a) shows SEM micrographs of the CaO—Al$_2$O$_3$ as-prepared. The calculated weight percents of CaO and Al$_2$O$_3$ are based on the total weight of CaO and Al$_2$O$_3$ and are based on EDX analysis.
Figure 3B:
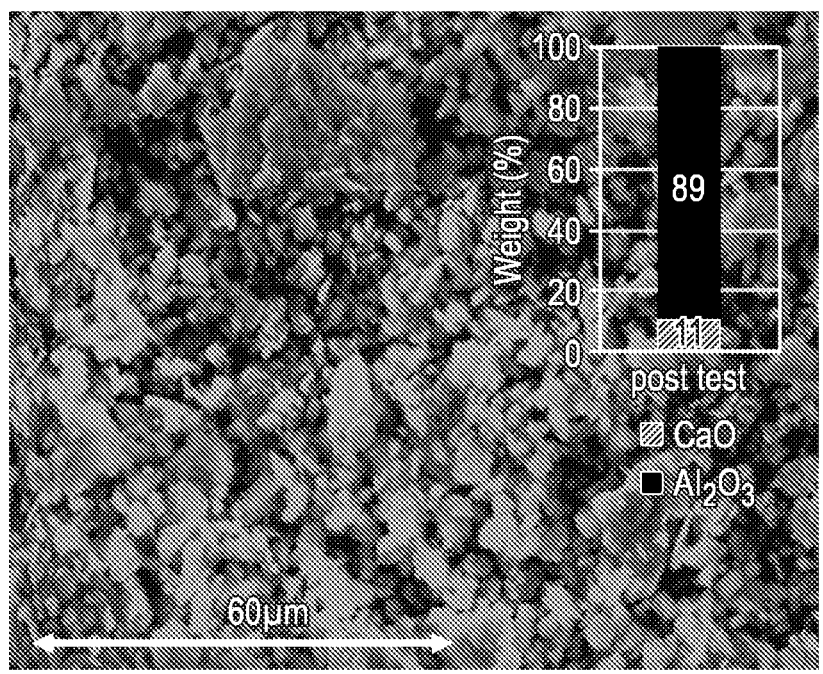
FIG. 3(b) shows SEM micrographs of the CaO—Al$_2$O$_3$ post-test, i.e. after the tests of Experiment 1. The calculated weight percents of CaO and Al$_2$O$_3$ are based on the total weight of CaO and Al$_2$O$_3$ and are based on EDX analysis.

FIG. 3 shows the SEM micrographs of the $CaO-Al_2O_3$ catalyst before and after the recyclability test. No significant changes were observed to the catalysts microstructure and CaO was uniformly coated on the surface of the $Al_2O_3$ support. However, the EDX analyses suggested a decrease of the Ca content, of approximately 58%. According to the EDX results, the CaO weight % was calculated and from the initial 21%, only 11% of CaO remained on the surface of the catalyst. These results are in good agreement with the XRD analysis that showed the decrease of the CaO phase and suggest that Ca leaching took place and led to the deactivation of the catalyst after 2 successful tests.

Figure 4A:
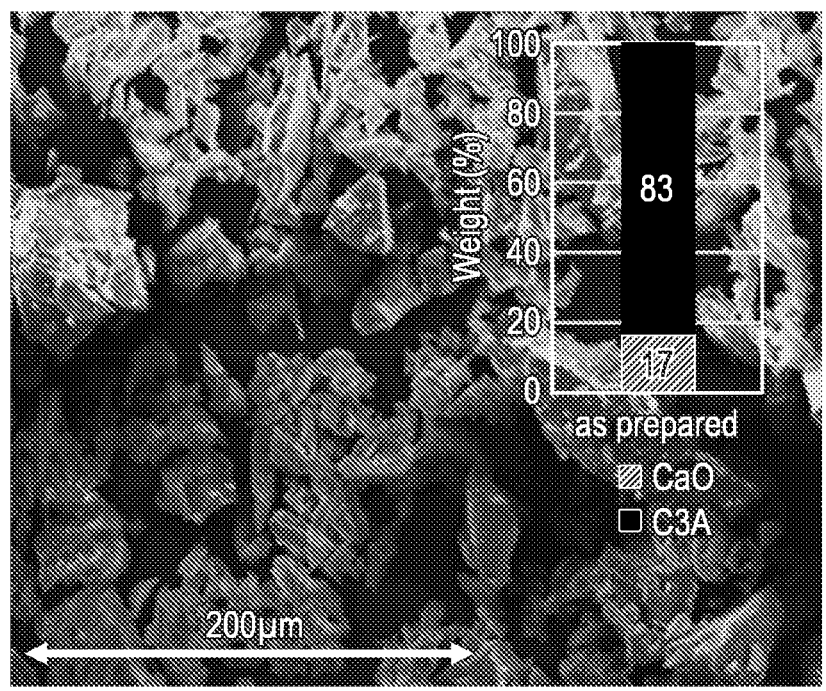
FIG. 4(a) shows SEM micrographs of the 2Ca/Al composite as-prepared. The calculated weight percents of CaO and C3A are based on the total weight of CaO and C3A and are based on EDX analysis.
Figure 4B:
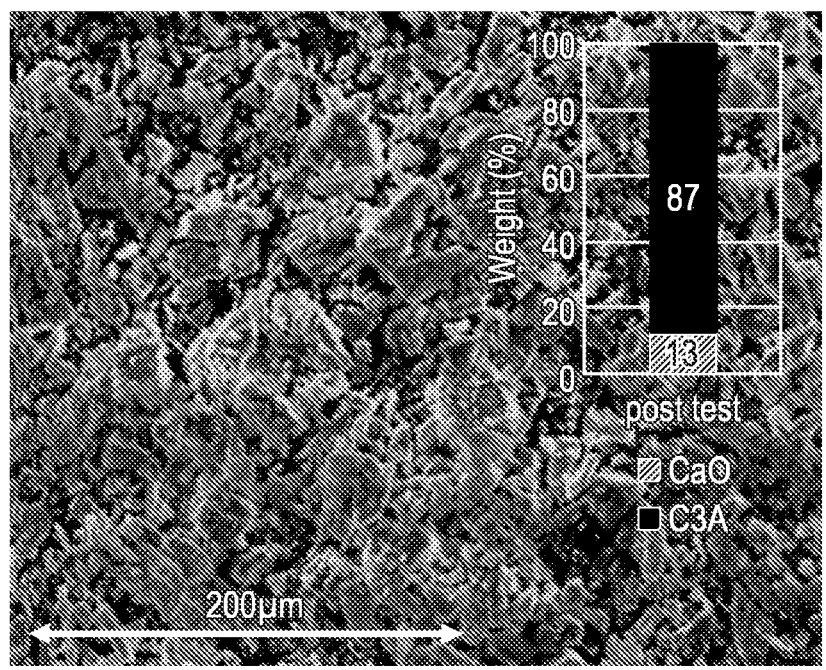
FIG. 4(b) shows SEM micrographs of the 2Ca/Al composite post-test, i.e. after the tests of Experiment 1. The calculated weight percents of CaO and C3A are based on the total weight of CaO and C3A and are based on EDX analysis.

FIG. 4 presents the microstructure of the CaO-C3A catalyst before and after the recyclability tests. The morphology of the particles of this catalyst was different than the CaO—$Al_2O_3$. The particles have larger particle size and they are more crystalline. Moreover, the CaO phase appeared to be mixed with the C3A phase and not deposited as a layer on the top of it. After the recyclability testing, the morphology of the particles was similar, but the particle size decreased probably due to the agitation that took place during the transesterification reaction that helped to break down the agglomerates. Moreover, the EDX results suggested a decrease of the Ca content of approximately 25%. Based on these results the CaO weight % was calculated and the CaO content decreased from 17 to 13 wt %. Therefore, the extent of calcium leaching from this catalyst was lower than that of CaO—$Al_2O_3$, even though it was used successfully for 4 tests instead of 2.

Table 1 summarises the results from the EDX analyses and the Ca/Al molar ratio was calculated before and after the catalysts deactivation. For the CaO—$Al_2O_3$ catalyst the Ca/Al molar ratio dropped by approximately 60%. The 2Ca/Al catalyst demonstrated higher Ca/Al molar ratios due to the Ca present in the C3A phase. After the recyclability tests, the ratio dropped from 2.38 to 1.78, which was a 25% decrease. For both catalysts the Ca/Al ratio decreased due to Ca leaching and led to the catalysts deactivation. The Ca leaching was also confirmed by the XRD analyses that showed the decrease of the CaO peaks.

This deactivation process was slower for the 2Ca/Al catalyst than the CaO—$Al_2O_3$. The first catalyst was successfully recycled for 4 times, while the second for just 2. This difference in the catalyst recyclability was due to the samples microstructure and preparation. The CaO—C3A catalyst was more stable, because CaO and C3A phases were homogeneously mixed. On the other hand, for the sample prepared by incipient wetness impregnation, the CaO phase formed a layer on the surface of the $Al_2O_3$ support. This catalyst was less stable and deactivated faster due to Ca leaching, because of the weaker interaction between CaO and $Al_2O_3$.

TABLE 1

Summary of the Ca/Al molar ratios of the catalysts before and after the recyclability tests and number of successful cycles performed

| Catalyst | Ca/Al molar ratio of fresh catalyst | Ca/Al molar ratio post-test | Tests performed |
| --- | --- | --- | --- |
| CaO-$Al_2O_3$ | 0.46* | 0.19* | 2 |
| 2Ca/Al | 2.38* (2.0)** | 1.78* (1.4)** | 4 |

*as calculated using EDX
**as calculated using ICP-OES

In summary, the XRD and EDX analyses suggest that Ca leaching is hindered by the presence of the $Ca_3Al_2O_6$ phase and that the catalyst lifetime is increased (i.e. the catalyst is more stable), as the CaO—$Ca_3Al_2O_6$ composite performed successfully with over 90% biodiesel yield for 4 cycles.

Experiment 2

Figure 5A:
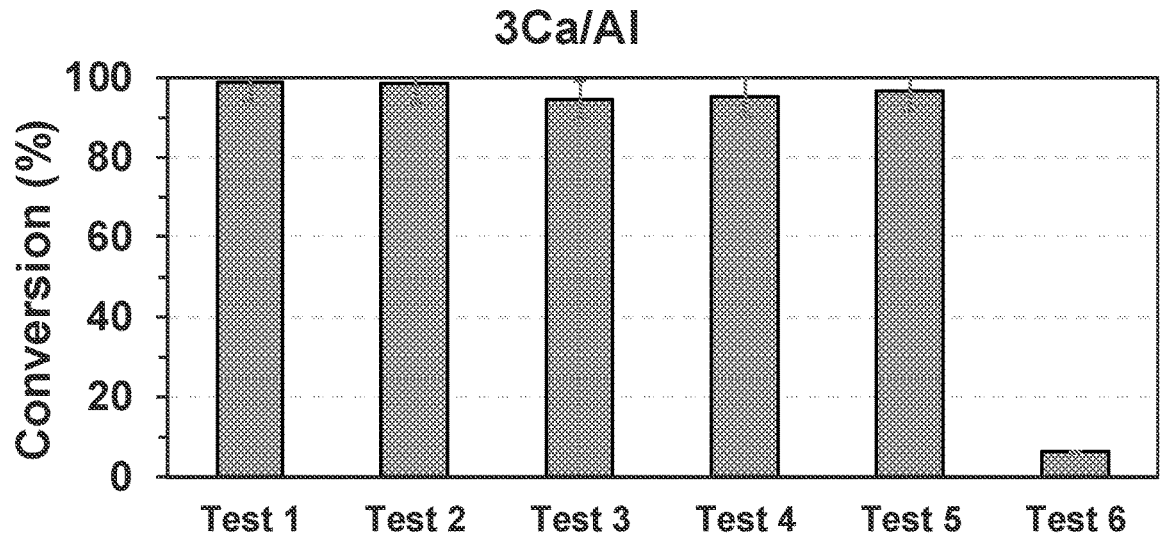
FIG. 5 (a) shows the triglycerides conversion to biodiesel and catalyst reusability during the transesterification reaction of cod liver oil with methanol using the 3Ca/Al composite as a catalyst.
Figure 5B:
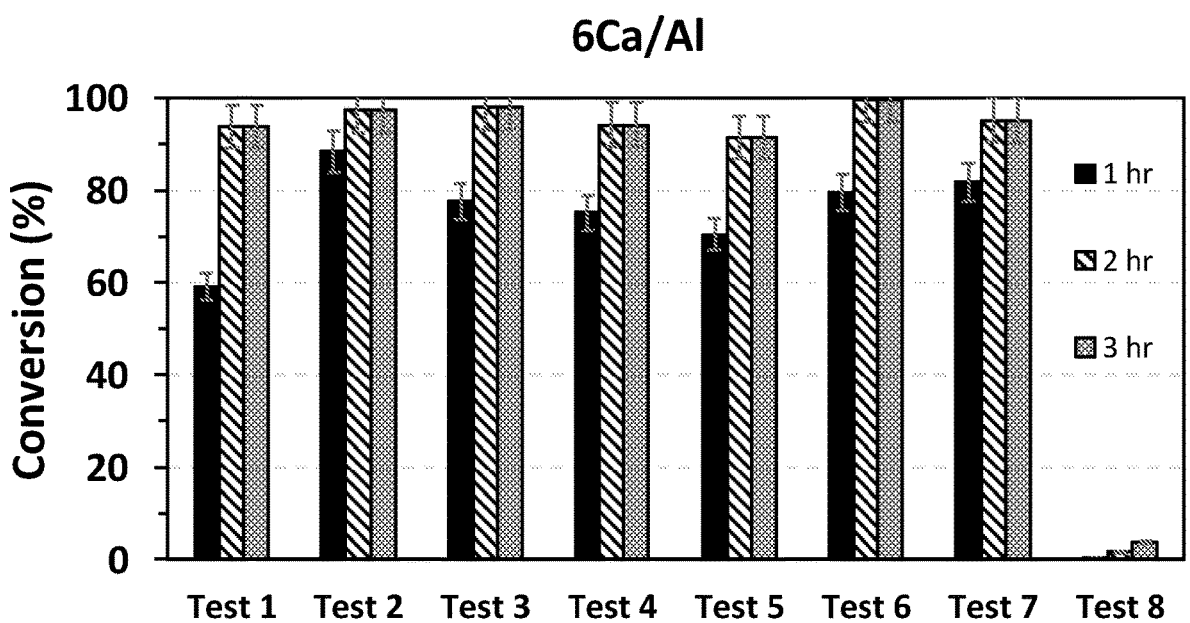
Figure 5C:
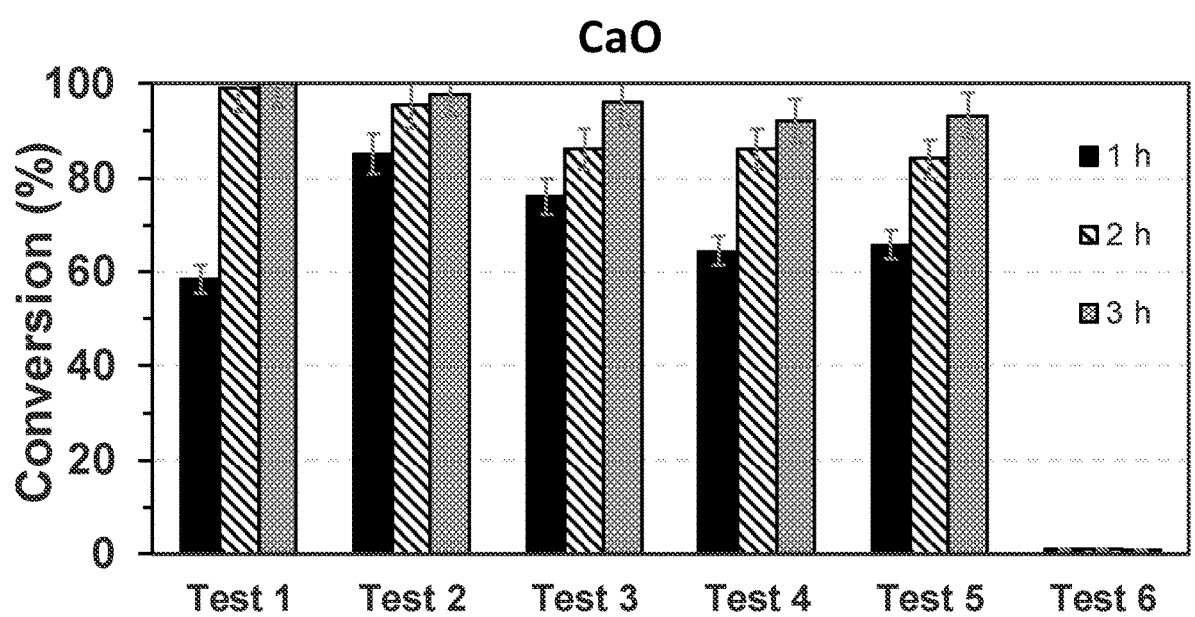

The catalytic activity of each of the second to sixth catalysts was evaluated based on the biodiesel yield during the transesterification reaction of fish oil triglycerides, operating at the reaction conditions described above. FIG. 5 shows the evolution of the biodiesel yield in hourly time intervals, until the reaction reached over 90% conversion, and the recyclability of the four different catalysts. Comparing the activity of the four catalysts, the 6Ca/Al composite performs best in terms of performance and recyclability. The 6Ca/Al composite was not fully deactivated until test 8.

XRD Analysis

Figure 6:
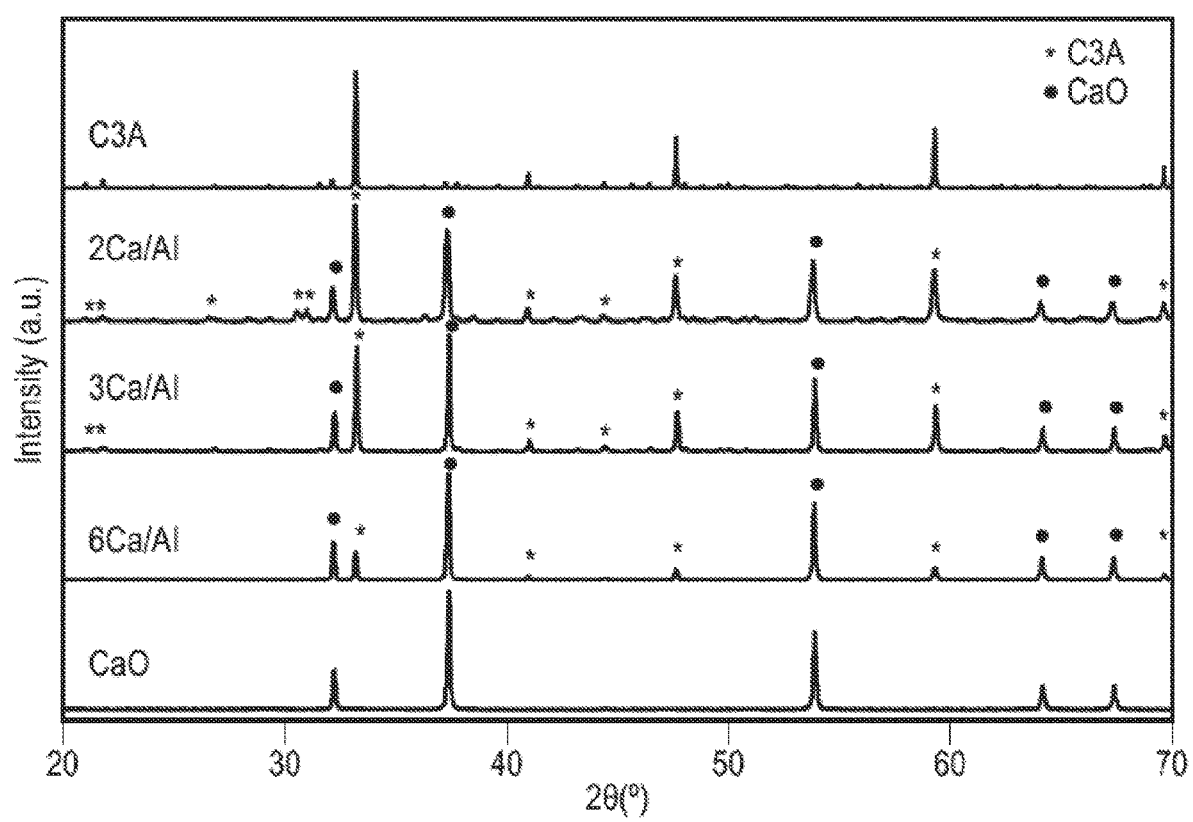
FIG. 6 shows the XRD patterns of the as-prepared C3A, 2Ca/Al composite, 3Ca/Al composite, 6Ca/A composite and CaO powder.
Figure 7A:
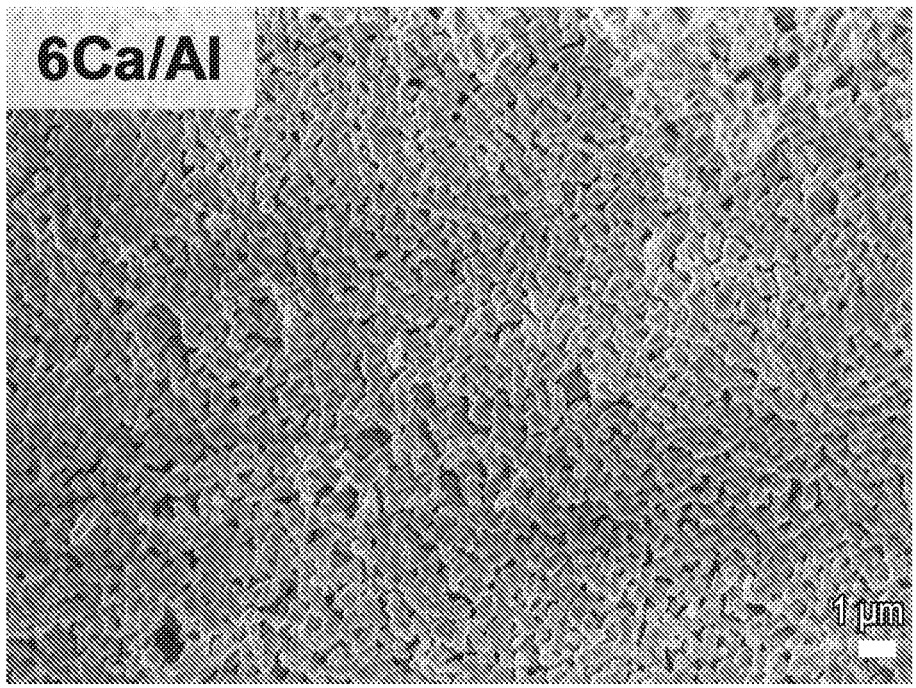
FIG. 7 (a) shows the SEM micrograph of the as-prepared 6Ca/Al composite.
Figure 7B:
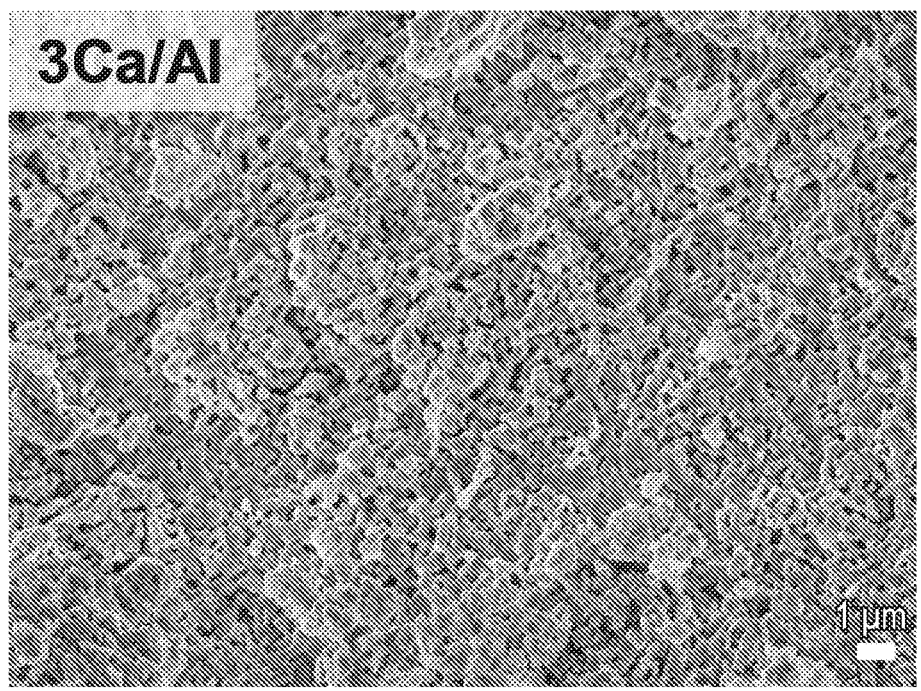
Figure 7C:
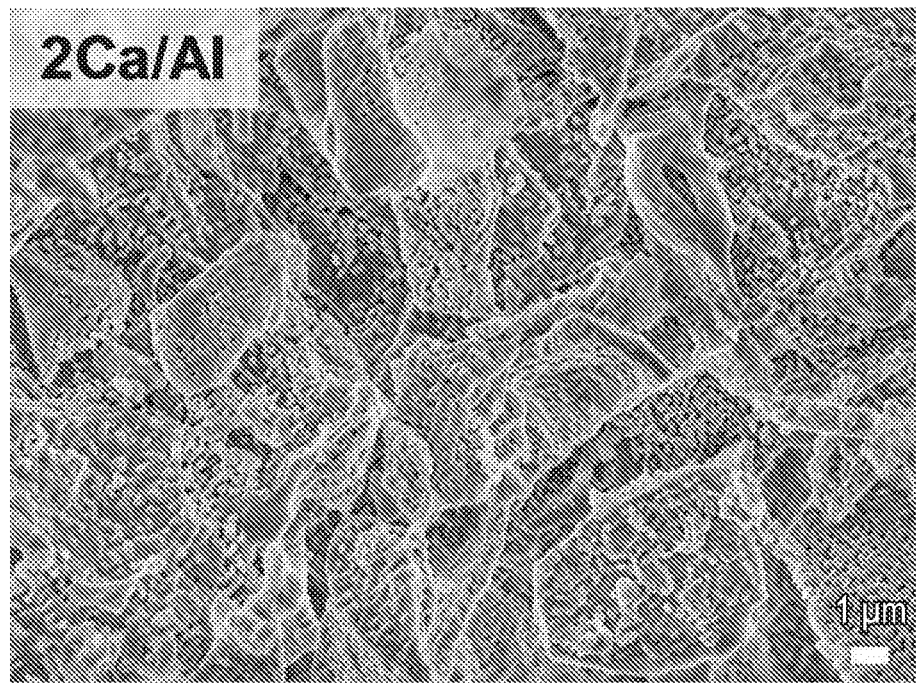
Figure 7D:
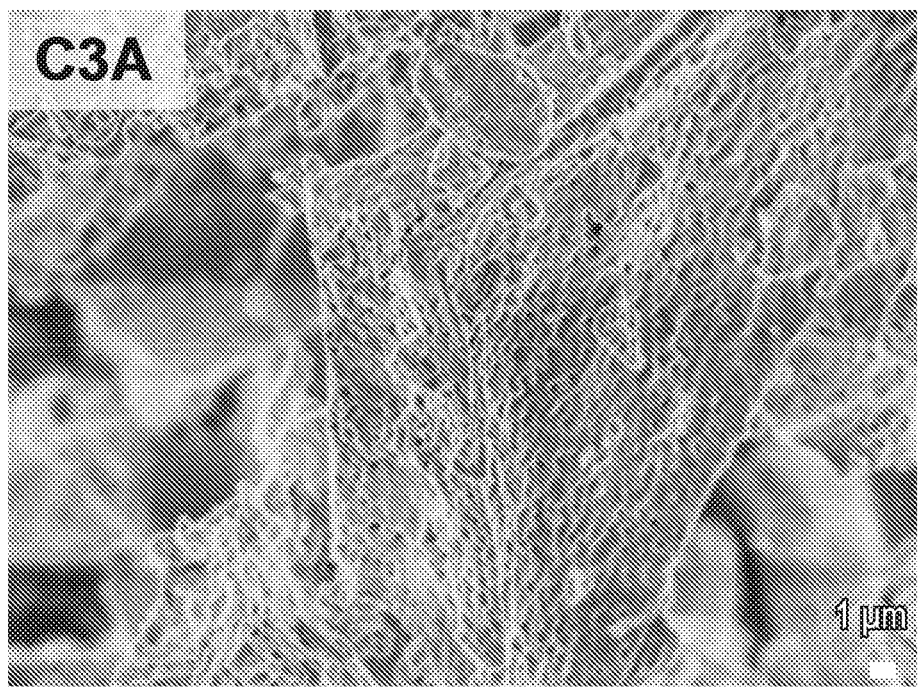

FIG. 6 presents the XRD patterns of the as-prepared catalysts. From this graph, it can be seen how the catalysts crystal structure changes when the Ca/Al ratio is altered. More specifically, by decreasing the Ca/Al molar ratio, the formation of the C3A phase is increased and the CaO phase is decreased. Finally, there is no evidence of any other phases formed between the two oxides.

FIG. 7 shows the morphology of the as-prepared catalysts with the different Ca/Al ratios. By increasing the Al content, the formation of the C3A phase is more evident, as it can be seen by the larger particles that appear on the sample. Consequently, the formation of the CaO phase is decreased and the CaO particles can form a layer on the top of the C3A particles. Therefore, for high Ca/Al ratios, the two phases are mixed uniformly, but for lower ratios, (2Ca/Al), the CaO is coated on the surface of the C3A particles.

Figure 8:
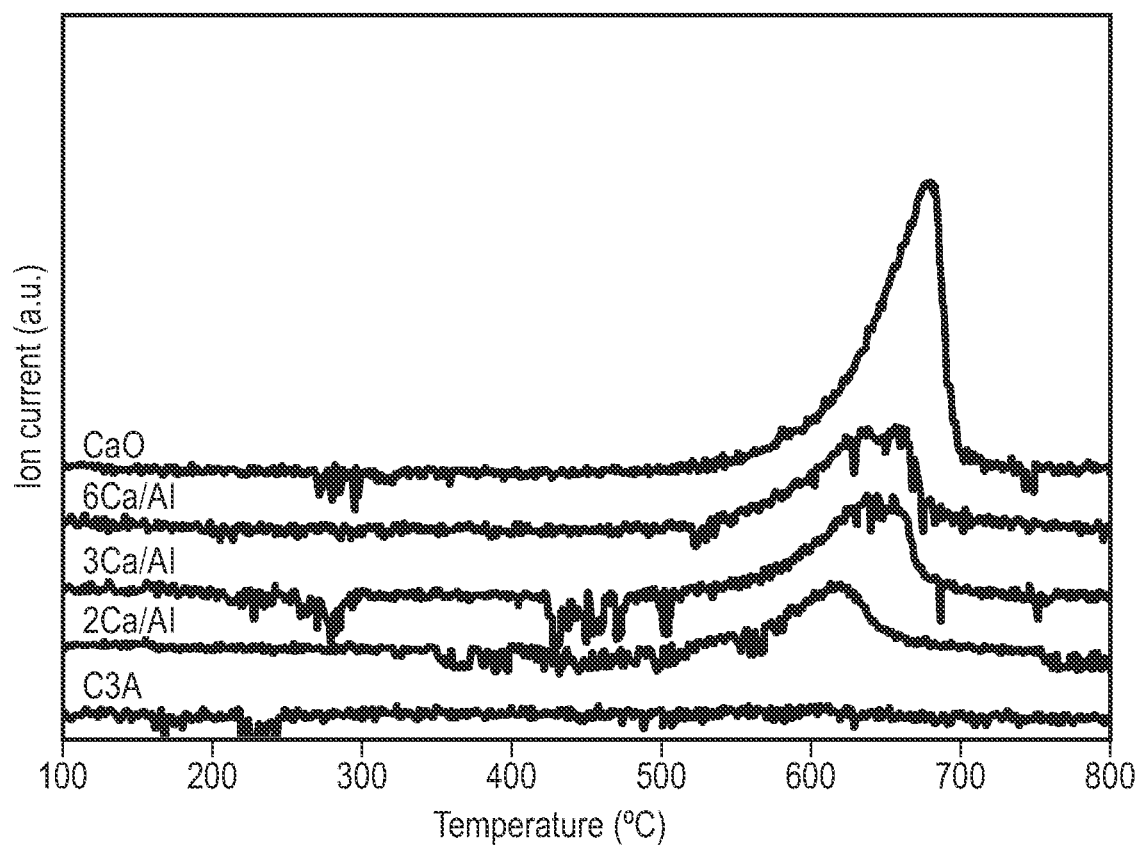
FIG. 8 shows the $CO_2$ desorption profiles of the C3A, 2Ca/Al composite, 3Ca/Al composite, 6Ca/Al composite and CaO.

FIG. 8 shows presents the $CO_2$ gas evolution when the $CO_2$ desorption took place between 100 and 800° C., as it was recorded by the MS. The strongest $CO_2$ signal was detected for CaO at 670° C. By decreasing the Ca/Al ratio from 6 to 2, the $CO_2$ signal deceases and a slight shift to lower temperatures takes place. Finally, no $CO_2$ signal was detected for C3A. Therefore, the higher the Ca/Al ratio is the more basic the catalyst will be.

Figure 9:
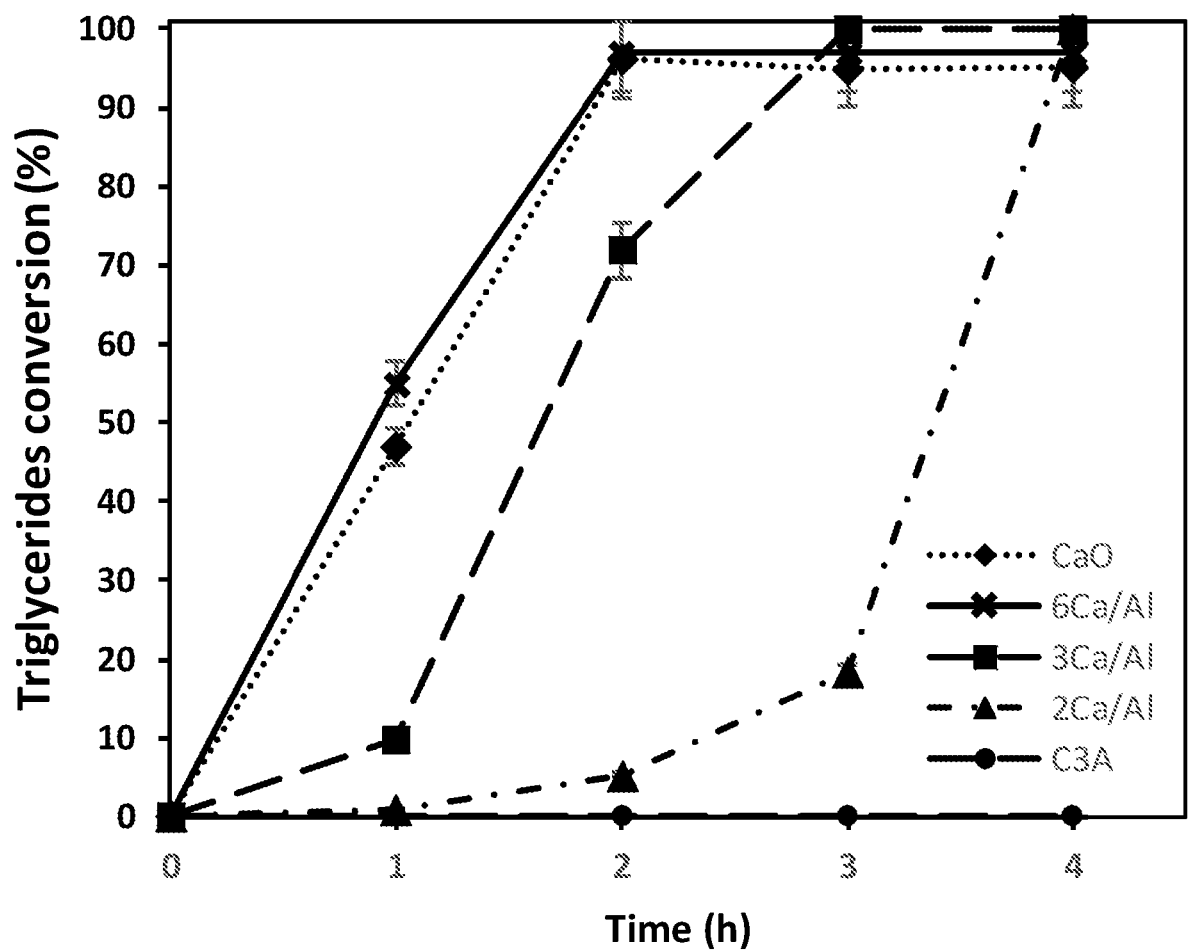
FIG. 9 shows the evolution of the transesterification reaction with time using the C3A, 2Ca/Al composite, 3Ca/Al composite, 6Ca/A composite and CaO as catalysts.

FIG. 9 shows the catalytic activity of the different catalysts for the transesterification reaction of cod liver oil to biodiesel. The samples were tested at the same reaction conditions in order to compare their catalytic activity. The reaction was carried out at 65° C., with 1:12 oil to methanol molar ratio and 800 rpm stirring. The amount of catalyst used was fixed at 10 wt % based on the oil used. FIG. 9 presents the evolution of the transesterification reaction with time for the synthesized catalysts. The conversion of the cod liver oil triglycerides to methyl esters in different time intervals was calculated by $H^1$ NMR. According to FIG. 9, all the catalysts demonstrated conversion higher than 95% after maximum 4 hr of reaction time, except C3A. Notably, the reaction rates differ and they are proportional to the Ca/Al ratio. More specifically, no conversion was observed for C3A. The slowest reaction rate was demonstrated by 2Ca/Al and full conversion was achieved at 4 hr. Following that, 3Ca/Al showed full conversion after 3 hr and then 6Ca/Al at 2 hr. Finally, pure CaO demonstrated full conversion at 2 hr, which was similar with 6Ca/Al.

The differences in the catalysts activity is related to their basicity. The more basic sites the catalyst has the faster the reaction rate for the biodiesel production will be. This can be also confirmed by the $CO_2$ TPD results in FIG. 8. Therefore, C3A which demonstrated no $CO_2$ adsorption, didn't present any FAMEs conversion. By increasing the Ca/Al ratio of the catalyst and consequently creating more basic sites in the catalyst, the catalytic activity increased, and the transesterification reaction took place faster. It is noteworthy that 6Ca/Al catalyst performed with similar reaction rates as pure CaO.

The invention claimed is:

1. A mixed oxide composite comprising CaO and $Ca_3Al_2O_6$, wherein the composite is in the form of particles, wherein the particles are supported on a porous support.

2. A mixed oxide composite according to claim 1, wherein the amount of CaO and $Ca_3Al_2O_6$ in the composite is greater than 50 wt % of the total weight of the composite.

3. A mixed oxide composite according to claim 1, comprising CaO in an amount of from 10 to 75 wt % based on the total weight of CaO and $Ca_3Al_2O_6$.

4. A mixed oxide composite according to claim 1, wherein the particles have an average size of from 10 nm to 100 µm.

5. A mixed oxide composite according to claim 1, wherein the particles are moulded so as to form a self-supporting structure.

6. A mixed oxide composite according to claim 1, wherein the amount of CaO and $Ca_3Al_2O_6$ in the composite is greater than 60 wt % of the total weight of the composite.

7. A mixed oxide composite according to claim 1, wherein the amount of CaO and $Ca_3Al_2O_6$ in the composite is greater than 70 wt % of the total weight of the composite.

8. A mixed oxide composite according to claim 1, wherein the amount of CaO and $Ca_3Al_2O_6$ in the composite is greater than 80 wt % of the total weight of the composite.

9. A mixed oxide composite according to claim 1, wherein the amount of CaO and $Ca_3Al_2O_6$ in the composite is greater than 90 wt % of the total weight of the composite.

10. A mixed oxide composite according to claim 1, wherein the amount of CaO and $Ca_3Al_2O_6$ in the composite is greater than 95 wt % of the total weight of the composite.

11. A mixed oxide composite according to claim 1, wherein the amount of CaO and $Ca_3Al_2O_6$ in the composite is greater than 97 wt % of the total weight of the composite.

12. A mixed oxide composite according to claim 1, comprising CaO in an amount of from 25 to 75 wt based on the total weight of CaO and $Ca_3Al_2O_6$.

13. A mixed oxide composite according to claim 1, comprising CaO in an amount of from 35 to 70 wt % based on the total weight of CaO and $Ca_3Al_2O_6$.

14. A mixed oxide composite according to claim 1, wherein the particles are moulded so as to form a honeycomb structure.

15. A method for preparing a mixed oxide composite, said method comprising:
   (a) heating an aqueous solution comprising (i) aluminium nitrate or aluminium nitrate hydrate, (ii) calcium nitrate or calcium nitrate hydrate, and (iii) an organic fuel until the solution combusts to form a powder; and
   (b) calcining the powder at a temperature of from 1000° C. or higher.

16. A method according to claim 15, wherein step (a) comprises heating the aqueous solution comprising aluminium nitrate or aluminium nitrate hydrate, calcium nitrate or calcium nitrate hydrate and an organic fuel so as to evaporate water and form a gel, followed by heating the gel until it combusts to form a powder.

17. A method according to claim 15, wherein the organic fuel is ethylene glycol, citric acid, urea, glycine, sucrose or mixtures thereof.

18. A method according to claim 17, wherein the organic fuel is a mixture of ethylene glycol and citric acid.

19. A method according to claim 18, comprising:
   (a) diluting $Ca(NO_3)_2 \cdot 4H_2O$ and $Al(NO_3)_2 \cdot 9H_2O$ in deionised water with ethylene glycol and citric acid to form an aqueous solution; heating the solution under stirring at a temperature of 100° C. so as to evaporate the water and form a gel; heating the gel to a temperature of from 250 to 500° C. so as to combust the gel and form a powder; and
   (b) calcining the powder at a temperature of from 1000 to 1300° C. for 2 to 12 hours.

20. A mixed oxide composite obtained by the method of claim 15.

21. A method of activating a mixed oxide composite comprising CaO and $Ca_3Al_2O_6$, comprising heating a C1 to C4 alcohol with glycerol in the presence of the mixed oxide composite so as to form calcium diglyceroxide.

22. An activated mixed oxide composite obtained by the method of claim 21.

23. A method for producing fatty acid alkyl esters comprising reacting a feedstock comprising fatty acid monoglycerides, diglycerides or triglycerides with a C1 to C4 alcohol in the presence of a mixed oxide composite comprising CaO and $Ca_3Al_2O_6$, or an activated mixed oxide composite according to claim 22.

24. A method according to claim 23, wherein the feedstock comprises a plant oil or an animal fat or oil.

25. A method according to claim 23, wherein the process further comprises recovering the mixed oxide composite from the reaction mixture.

26. A method according to claim 25, wherein recovering the mixed oxide composite from the reaction mixture comprises separating the composite from the reaction mixture, washing and drying the composite and, wherein the method further comprises reusing the composite for producing fatty acid alkyl esters.

27. A method according to claim 23, wherein the feedstock comprises fatty acid triglycerides.

28. A method according to claim 23, wherein the alcohol is methanol or ethanol.

29. A method for the transesterification of monoglycerides, diglycerides or triglycerides comprising the steps of:
   heating a mixture of C1-C4 alcohol, glycerol and a mixed oxide catalyst comprising CaO and $Ca_3Al_2O_6$, so as to form at least calcium diglyceroxide;
   contacting the calcium diglyceroxide with monoglycerides, diglycerides or triglycerides; and
   transesterifying the monoglycerides, diglycerides or triglycerides.

30. A mixed oxide composite comprising CaO and $Ca_3Al_2O_6$, wherein the amount of CaO and $Ca_3Al_2O_6$ in the composite is 100 wt % of the total weight of the composite.

31. A mixed oxide composite comprising CaO and $Ca_3Al_2O_6$, wherein the composite is a uniformly dispersed mixture of CaO and $Ca_3Al_2O_6$.

* * * * *